(12) United States Patent
Sauve et al.

(10) Patent No.: US 7,504,489 B2
(45) Date of Patent: Mar. 17, 2009

(54) INHIBITORS OF ADP-RIBOSYL TRANSFERASES, CYCLASES, AND HYDROLASES, AND USES THEREOF

(75) Inventors: Anthony A. Sauve, Bronx, NY (US); Vern L. Schramm, New Rochelle, NY (US)

(73) Assignee: Albert Einstein College of Medicine of Yeshiva University, Bronx, NY (US)

(*) Notice: Subject to any disclaimer, the term of this patent is extended or adjusted under 35 U.S.C. 154(b) by 0 days.

(21) Appl. No.: 11/294,932

(22) Filed: Dec. 5, 2005

(65) Prior Publication Data

US 2006/0084616 A1    Apr. 20, 2006

Related U.S. Application Data

(63) Continuation of application No. 10/038,760, filed on Jan. 4, 2002, now Pat. No. 7,056,894.

(60) Provisional application No. 60/259,720, filed on Jan. 4, 2001.

(51) Int. Cl.
| | |
|---|---|
| C07H 15/00 | (2006.01) |
| C07H 17/00 | (2006.01) |
| C07H 17/02 | (2006.01) |
| C07G 3/00 | (2006.01) |
| C07G 11/00 | (2006.01) |

(52) U.S. Cl. .................. 536/17.2; 536/4.1; 536/17.3; 536/17.4; 536/17.5; 536/18.4

(58) Field of Classification Search ................ 536/4.1
See application file for complete search history.

(56) References Cited

U.S. PATENT DOCUMENTS

| 5,569,650 A | 10/1996 | Watanabe et al. |
| 5,679,394 A | 10/1997 | Long, Jr. et al. |
| 6,103,701 A | 8/2000 | Von Borstel et al. |
| 7,022,680 B2 | 4/2006 | Sauve et al. |
| 7,056,894 B2 | 6/2006 | Sauve et al. |
| 2006/0089318 A1 | 4/2006 | Sauve et al. |
| 2006/0094670 A1 | 5/2006 | Sauve et al. |

FOREIGN PATENT DOCUMENTS

WO    WO 97/31008    *    8/1997

OTHER PUBLICATIONS

Sujino et al., Facile Synthesis of 2';3'-unsaturated Nucleosides from 2-Deoxyribose, Tetrahedron Letters, 34(34), pp. 6133-6136, 1996.*
Sanghvi et al., Synthesis of Certain Exocyclic Thiazole Nucleosides Related to Tiazofurin, J Heterocyclic Chem., 25, pp. 623-633, 1988.*
Luo et al., Oxidative Damage to DNA Constituents by Iron-mediated Fenton Reactions, Journal of Biological Chemistry, 271(35), pp. 21167-21176, 1996.*
Heller et al. ("Heterocyclic glycosyl derivatives", Pharmazie, 1973, 28(10), 641-7—as cited in CAPLUS Abstract No. 1974:83508).*
Kaneko et al. ("Substrate Specificity of the α-L-Arabinofuranosidase from *Trichoderma reesei*", Biosci. Biotechnol. Biochem., 62(11), 2205-2210, 1998).*
Sujino et al., Facile Synthesis of 2'3'-Unsaturated Nucleosides from 2-Deoxyribose, Tetrahedron Letters, 1996, vol. 37(34) pp. 6133-6136.*
Heller et al., Synthese von 2'-desocy-D-ribofuranosiden von 3-Mercaptopyridazinen/Thiopyridazonen-(3), Pharmazie, 28(10), 1973.*
Sauve et al., entitled "A covalent intermediate in CD38 is responsible for ADP ribosylation and cyclization reactions," J. of the American Chemical Society, vol. 122, Nol. 33, Aug. 23, 2000, pp. 7855-7859.
Togo et al., entitled "A facile preparative method of c-nucleosides," Chemistry Letters, vol. 9, 1992, pp. 1673-1676.
Ashamu et al., entitled "Roles for adenosine ribose hydroxyl groups in cyclic adenosine 5'-diphosphate ribose-mediated Ca2+ release," Biochemistry, 1997, 36:9509-9517.
Bailey et al., entitled "Cyclic aristeromycin diphosphate ribose: a potent and porrly hydrolysable Ca2+-mobilising mimic of cyclic adenosine diphoshate ribose," FEBS Lett., 379:227-230 (1996).

(Continued)

Primary Examiner—Traviss C McIntosh, III
(74) Attorney, Agent, or Firm—Amster, Rothstein & Ebenstein LLP

(57) ABSTRACT

The present invention provides compounds having the formula:

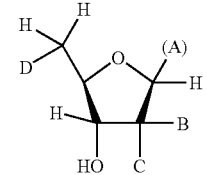

wherein A is chosen from a nitrogen-, oxygen-, or sulfur-linked aryl, alkyl, cyclic, or heterocyclic group; both B and C are hydrogen, or either B or C is a halogen, amino, or thiol group and the other of B or C is hydrogen; and D is a primary alcohol, a hydrogen, or an oxygen, nitrogen, carbon, or sulfur linked to phosphate, a phosphoryl group, a pyrophosphoryl group, or adenosine monophosphate through a phosphodiester or carbon-, nitrogen-, or sulfur-substituted phosphodiester bridge, or to adenosine diphosphate through a phosphodiester or carbon-, nitrogen-, or sulfur-substituted pyrophosphodiester bridge.

The present invention also provides pharmaceutical compositions containing the above compounds, methods of using the above compounds as pharmaceuticals, and processes for preparing the above compounds.

Also provided are methods for inhibiting an ADP-ribosyl transferase, ADP-ribosyl cyclase, or ADP-ribosyl hydrolase enzyme, and methods for treating a disease or condition associated with an ADP-ribosyl transferase, ADP-ribosyl cyclase, or ADP-ribosyl hydrolase enzyme in a subject in need of treatment thereof.

9 Claims, 9 Drawing Sheets

OTHER PUBLICATIONS

Clapper et al., entitled "Pyridine nucleotide metabolittes stimulate calcium release from sea urchin egg microsomes desensitized to inositol trisphophate." J Biol. Chem., 1987, 262:9561-9568.

Fernandez et al., entitled "Analysis of the distribution of huan CD38 and of its ligand CD31 in the normal tissues," J. Biol. Regul. Homestatic Agents, 1998, 12:81-91.

Fox et al., entitled "Nucleosides. XIII. Direct synthesis of 2'-deoxycytidine and its alpha-anomer," J. Am. Chem. Soc., 1961, 83:4066-4070.

Handlon and Oppenheimer, entitled "Substituent effect of the pH-independent hydrolysis of 2'-substituted nicotinamide arabinosides," J. Org. Chem., 1991, 56:5009-5010.

Hara-Yokoyama et al., entitled "Complex gangliosies as cell surface inhibitors from the Ecto-NAD+ glycohydrolase of CD38," Biochemistry, 2001, 40:888-895.

Howard et al., entitled "Formation and hydrolysis of cyclic ADP-ribose catalyzed by lymphocyte antigen CD38," Science, 1993, 262:1056-1059.

Mehta, et al., entitled "Human CD38, a cell-surface protein with multiple functions," The FASEB Journal, Oct. 1996, 10:1408-17.

Lee, et al., entitled "Structural Determination of a Cyclic Metabolite of NAD+ with Intracellular Ca2+-mobilizing Activity," J. Biol. Chem., Jan. 1989, 264:1608-15.

Prasad, et al., entitled "Crystal structure of Aplysia ADP ribosyl cyclase, a homologue of the bifunctional ectozyme CD38," Nat. Struct. Biol., Nov. 1996, 3:957-64.

Lee, et al., entitled "The crystal structure of cyclic ADP-ribose," Nature Struct. Biol., Mar. 1994, 1:143-44.

Reyes-Harde, et al., "Evidence of a role for cyclic ADP-ribose in long-term synaptic depression in hippocampus," Proc. Natl. Acad. Sci. USA, Mar. 1999, 96:4061-66.

Galione, et al., entitled "Ca2+-Induced Ca2+ Release in Sea Urchin Egg Homogenates: Modulation by Cyclic ADP-Ribose," Science, Sep. 1991, 253:1143-46.

Okamoto H., entitled "The CD38-cyclic ADP-ribose signaling system in insulin secretion," Mol. Cell. Biochem., Mar. 1999, 193:115-18.

Cockayne, et al., entitled "Mice Deficient for the Ecto-Nicotinamide Adenine Dinucleotide Glycohydrolase CD38 Exhibit Altered Humoral Immune Responses," Blood, Aug. 1998, 92:1324-33.

Sauvé, et al., entitled "The Reaction Mechanism for CD38. A Single Intermediate Is Responsible for Cyclization, Hydrolysis, and Base-Exchange Chemistries," Biochemistry, Sep. 1998, 37:13239-49.

Muller-Steffner, et al., "Mechanism of Cyclization of Pyridine Nucleotides by Bovine Spleen NAD+ Glycohydrolase," J. Biol. Chem., Sep. 1996, 271:23967-72.

Berthelier, et al., entitled "Human CD38 is an authentic NAD(P)+ glycohydrolase," Biochem. J., Mar. 1998, 330:1383-90.

Kim, et al., entitled "Synthesis and Degradation of Cyclic ADP-Ribose by NAD Gyclohydrolases," Science, Sep. 1993, 261;1330-33.

Niedballa and Vorbrüggen, entitled "A General Synthesis of N-Glycosides. I. 1 Synthesis of Pyrimidine Nucleosides," J. Org. Chem., Dec. 1974, 39:3654-60.

Morrison and Walsh, entitled "The Behavior and Significance of Slow-Binding Enzyme Inhibitors," Adv. Enzymol. Relat. Areas Mol. Biol., 1988, 61:201-301.

Porter, et al., entitled "Identification of the Active Site Nucleophile in Nucleoside 2-Deoxyribosyltransferase as Glutamic Acid 98," J. Biol. Chem., Jun. 1995, 270:15551-56.

Zechel and Withers, entitled "Glycosidase Mechanisms: Anatomy of a Finely Tuned Catalyst," Acc. Chem Res., 2000, 33:11-18.

Wong, et al., entitled "Identification of Glu-540 as the Catalytic Nucleophile of Human beta-Glucuronidase Using Electrospray Mass Spectrom," J. Bio. Chem., Dec. 1998, 273;34057-62.

Withers and Street, entitled "Identification of a Covalent alpha-D-Glucopyranosyl Enzyme Intermediate Formed on a beta-Glucosidase," J. Am. Chem. Soc., Dec. 1988, 110:8551-53.

Muller-Steffner, et al., entitled "Slow-binding Inhibition of NAD+ Glycohydrolase by Arabino Analogues of beta-NAD+," J. Biol. Chem., May 1992, 267:9606-11.

Berthelier, et al., entitled "Probing ligand-induced conformational changes of human CD38," Eur. J. Biochem., May 2000, 267(10):3056-64.

Merkler, et al., entitled "The Rate Constant Describing Slow-Onset Inhibition of Yeast AMP Deaminase by Coformycin Analogues Is Independent of Inhibitor Structure," Sep. 1990, Biochemistry, 29:8358-64.

Lund, et al., entitled "CD38: a new paradigm in lymphocyte activation and signal transduction," Immunol. Rev., Feb. 1998, 161:79-93.

Lee, et al., entitled "Structures and activities of cyclic ADP-ribose, NAADP and their metabolic enzymes," Mol. Cell. Biochem., Mar. 1999, 193:89-98.

Lee, H.C., entitled "Modulator and Messenger Functions of Cyclic ADP-Ribose in Calcium Signaling," Recent Prog. Horm. Res., 1996, 51:355-88.

Lee, H.C., entitled "Physiological Functions of Cyclic ADP-Ribose adn NAADP as Calcium Messenger," Annu. Rev. Pharmacol. Toxicol., 2001, 41:317-45.

Itoh et al., entitled "Molecular cloning of murine BST-1 having homology with CD38 and aplysia ADP-ribosyl cyclase," Biochem. Biophys. Res. Commun., 1994, 203:1309-1317.

Jackson and Bell, entitled "Isolation of a cDNA encoding the human CD38 (T10) molecule, a cell surface glycoprotein with an unusual discontinuous pattern of expression during lymphocycle differentiation," J. Immunol., 1990, 144:2811-2815.

Jiang et al.,entitled "Membrane-permeant esters of phosphatidylinositol 3,4,5-trisphosphate," J. Biol. Chem., 1998, 273:11017-11024.

Kaisho et al., entitled "BST-1, a surface molecule of bone marrow stromal cell lines that facilitates pre-B-cell growth," Proc. Natl. Acad. Sci. USA, 1994, 91:5325-5329.

Kang et al., entitled "Synthesis and biological activity of bis(pivaloyloxymethyl) ester of 2'-azido-2'deoxyuridine 5'-monophosphate," Nucleosides & Nurcleotides, 1998, 17:1089-1098.

Kato et al., entiteld "Regulatory role of CD38 (ADP-ribosyl cyclase/ cyclic ADP-ribose hydrolase) in insulin secretion by glucose in pancreatic beta-cells," J. Biol. Chem., 1995, 270:30045-30050.

Khoo and Chang, entitled "Localization of plasma membrane CD38 is domain specific in rat hepatocyte," Arch. Biochem. Biophys., 2000, 373:35-43.

Kruppa et al., entitled "Bioactivatable derivatives of 8-substituted cAMP-analogues." Bioorg. Med. Chem. Lett., 1997, 7:945-948.

Lee and Aarhus, entitled "ADP-ribosyl cyclase: an enzyme that cyclizes NAD+ into a calcium-mobilizing metabolite," Cell Regul., 1991, 2:203-209.

Lee and Aarhus, entitled "Fluorescent analogs of NAADP with calcium mobilizing activity," Biochem. Biophys. Acta., 1998, 1425:263-271.

Li et al., entitled "Membrane-permeant esters of inositol polysphosphates, chemical syntheses and biological applications." Tetrahedron, 1997, 53:12017-12040.

Mizuguchi et al., entitled "Neuronal localization of CD38 antigen in the human brain." Brain Res., 1995, 697:235-240.

Munshi et al., entiteld "Characterization of the active site of ADP-ribosyl cyclase," J. Biol. Chem., 1999, 274:30770-30777.

Normark et al., entitled "How neutrophils recognize bacteria and move toward infection," Nat. Med., 2001, 7:1182-1184.

Oppenheimer and Handlon, entitled "Mechanism of NAD-dependent enzymes," In The Enzyme, Sigman, D.L. Ed., Academic Press Inc.: San Diego CA, 1992, Chapter 10, 20:453-505.

Partida-Sanchez et al., entitled "Cyclic ADP-ribose production by CD38 regulates intracellular calcium release, extracellular calcium influx and chemotaxis in neutrophils and is required for bacterial clearance in vivo," Nat. Med., 2001, 7:1209-1216.

Rusinko and Lee, entitled "Widespread occurrence in animal tissues of an enzyme catalyzing the conversion of NAD+ into a cyclic metabolite with intracellular Ca2+-mobilizing activity," J. Biol. Chem., 1989, 264:11725-11731.

Sato et al., "Inhibitor peptide SNP-1 binds to soluble form of BST-1/CD157 at a 2:2 stoichiometry," Eur. J. Biochem., 1999, 264:439-445.

Sato et al., "Novel peptide inhibitor of ecto-ADP-ribosyl cyclase of bone marrow stromal cell antigen-1 (BST-1/CD157)," Biochem. J., 1999, 337:491-496.

Sethi et al., entitled "7-Deaza-8-bromo-cyclic ADP-ribose, the first membrane-permeant, hydrolysis-resistant cyclic ADP-ribose antagonist," J. Biol. Chem., 1997, 272:16358-16363.

Sleath et al., entitled "Pyridine coenzyme analogues. 3. Synthesis of three NAD+ analogues containing a 2'-deoxy-2'-substituted nicotinamide arabinofuranosyl moiety," J. Org. Chem., 1991, 56:3608-3613.

States et al., entitled "Similarities in amino acid sequences of aplysia ADP-ribosyl cyclase and human lymphocyte antigen CD38," Trends Biochem. Sci., 1992, 17:495-497.

Sun et al., entitled "CD38/ADP-ribosyl cyclase: a new role in the regulation of osteoclastic bone resorption," Cell. Biol., 1999, 146:1161-1171.

Wall et al., "Inhibition of the intrinsic NAD+ glycohydrolase activity of CD38 by carbocyclic NAD analogues." Biochem J., 1998, 335:631-636.

Walseth and Lee, entitled "Synthesis and characterization of antagonists of cyclic-ADP-ribose-induced Ca2+ release," Biochem. Biophys. Acta., 1993, 1178:235-242.

Walseth et al., "Identification of cyclic ADP-ribose-binding proteins by photoaffinity labeling," J. Biol. Chem., 1993, 268:26686-26691.

Wong et al., "Cyclic 3-deaza-adenosine diphosphoribose: a potent and stable analog of cyclic ADP-ribose." Biochem. Biophys. Acta, 1999, 1472:555-564.

Wu et al., entitled "Abscisic acid signaling through cyclic ADP-ribose in plants," Science, 1997, 278:2126-2130.

Yamamoto-Katayama et al., "Crystallographic studies on human BST-1/CD157 with ADP-ribosyl cyclase and NAD glycohydrolase activities." J. Mol. Biol., 316:711-723 (2002).

* cited by examiner

INHIBITORS OF ADP-RIBOSYL TRANSFERASES, CYCLASES, AND HYDROLASES, AND USES THEREOF This application is a continuation of application Ser. No. 10/038,760, filed Jan. 4, 2002, now U.S. Pat. No. 7,056,894, which claims the benefit of U.S. Provisional Application No. 60/259,720, filed Jan. 4, 2001.

STATEMENT OF GOVERNMENT INTEREST

This invention was made with government support under NIH Grant Nos. GM19335 and AI34342. As such, the United States government has certain rights in this invention.

BACKGROUND OF THE INVENTION

Human cyclic ADP-ribose synthetase (CD38) is an ectoenzyme, expressed on the surface of β cells, that makes cyclic-adenosine-diphosphate-ribose (cADPR) and ADP-ribose from nicotinamide-diphosphate-ribose (oxidized form) ($NAD^+$). Nicotinamide guanine dinucleotide ($NGD^+$) is also cyclized by CD38 to form cGDPR, and hydrolyzed to form GDPR. Human CD38 (1-2, 33) and *Aplysia californica* adenosine-diphosphate (ADP) ribosyl-cyclase (3-4, 34-35) share 68% homology in primary sequence (36); both synthesize cADPR from $NAD^+$ (15, 37). The compound cADPR is formed by intramolecular ADP-ribosylation at the N1 position of the adenine ring (5), and is a potent agent for calcium-ion ($Ca^{2+}$) release from intracellular $Ca^{2+}$ stores (1, 7, 38-44).

An increasing volume of evidence indicates that CD38 and ADP ribosyl-cyclase regulate important physiological processes in invertebrates (1, 38-44), plants (8), and mammals (1, 2, 6, 9-10, 45) via the synthesis of cADPR. In mammals, CD38 and cADPR have been implicated in the regulation of cellular processes, including insulin release (9), lymphocyte activation (2, 10), bone homeostasis (45), and synaptic plasticity (6). Additionally, the presence of CD38 has been linked to cytokine-induced differentiation (1), cell adhesion (1), and signal transduction (37). The wide distribution of CD38 in the brain, white blood cells, pancreas, and other tissues, suggests that this enzyme may have a general signaling role via cADPR production in vivo.

cADPR has been implicated in the release of $Ca^{2+}$ from inside cells (1, 7, 38-44). Mobilization of internal calcium is an important signaling mechanism in cells, and may be implicated in numerous pathologies. Diseases and conditions associated with the transmembrane flux of $Ca^{2+}$ ions into cells, particularly vascular smooth muscle cells, cardiac muscle cells, and cells of the nervous system, may include angina (e.g., angina pectoris, chronic stable angina, and vasospastic angina), arrhythmias, atrial fibrillation, hypertension, paroxysmal supraventricular tachycardia, adrenoleukodystrophy (ALD), and multiple sclerosis (MS).

Small-molecule, mechanism-based inhibitors of specific signaling pathways are desirable for therapeutic use. Unlike most conventional drugs, which temporarily inhibit the target enzyme, many mechanism-based inhibitors permanently disable the target enzyme. Small molecules that inhibit CD38 would be expected to decrease levels of cADPR, resulting in a modification in intracellular levels of $Ca^{2+}$. In particular, inhibition of cADPR-stimulated $Ca^{2+}$ release would be expected to have significant effects on calcium-mediated signaling pathways in many cells and tissues, thereby providing a useful treatment option for pathologies in which $Ca^{2+}$ regulation is implicated. However, prior to the present invention, there were no known effective, small-molecule, mechanism-based inhibitors of CD38 having the potential for regulation of cADPR levels.

SUMMARY OF THE INVENTION

The present invention is based upon the design and synthesis of a novel class of small-molecule, mechanism-based inhibitors of human CD38 that accomplish mechanism-based trapping at the enzyme's catalytic site. These inhibitors and their analogues provide new tools for investigating biological pathways in which CD38 and related enzymes are involved, and offer new therapeutic options for treating diseases and conditions associated with CD38, related enzymes, and cADPR. Accordingly, it is an object of the present invention to provide pharmaceuticals that are effective inhibitors of ADP-ribosyl cyclases, transferases, and hydrolases.

It is also an object of the present invention to provide compounds having the formula:

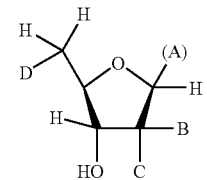

wherein A is chosen from a nitrogen-, oxygen-, or sulfur-linked aryl, alkyl, cyclic, or heterocyclic group; both B and C are hydrogen, or either B or C is a halogen, amino, or thiol group and the other of B or C is hydrogen; and D is a primary alcohol, a hydrogen, or an oxygen, nitrogen, carbon, or sulfur linked to phosphate, a phosphoryl group, a pyrophosphoryl group, or adenosine monophosphate through a phosphodiester or carbon-, nitrogen-, or sulfur-substituted phosphodiester bridge, or to adenosine diphosphate through a phosphodiester or carbon-, nitrogen-, or sulfur-substituted pyrophosphodiester bridge.

It is a further object of the present invention to provide pharmaceutical compositions containing the above compounds, methods of using the above compounds as pharmaceuticals, and processes for preparing the above compounds.

Additionally, it is an object of the present invention to provide methods for inhibiting an ADP-ribosyl transferase, ADP-ribosyl cyclase, or ADP-ribosyl hydrolase enzyme, by contacting the enzyme with one of the above compounds in an amount effective to inhibit the enzyme.

Finally, it is an object of the present invention to provide methods for treating a disease or condition associated with an ADP-ribosyl transferase, ADP-ribosyl cyclase, or ADP-ribosyl hydrolase enzyme in a subject in need of treatment thereof, by administering to the subject one of the above compounds in an amount effective to treat the disease or condition.

Additional objects of the present invention will be apparent in view of the description which follows.

DETAILED DESCRIPTION OF THE INVENTION

Figure 1:
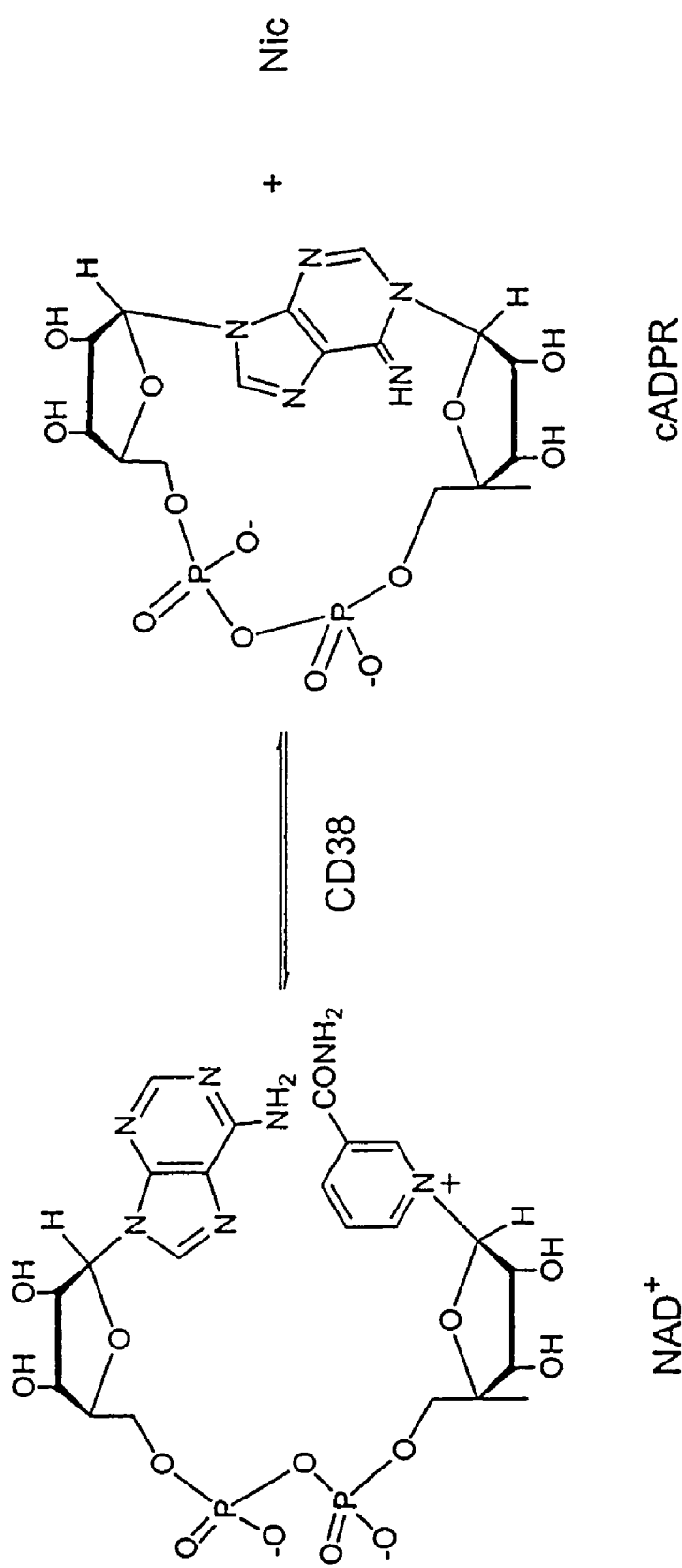
FIG. 1 illustrates the stoichiometry of cADPR synthesis from $NAD^+$ catalyzed by CD38.

In one aspect, the present invention provides inhibitor compounds having the formula:

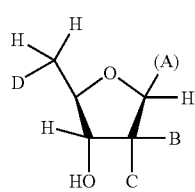

formula (I)

wherein A is chosen from a nitrogen-, oxygen-, or sulfur-linked aryl, alkyl, cyclic, or heterocyclic group; both B and C are hydrogen, or either B or C is a halogen, amino, or thiol group and the other of B or C is hydrogen; and D is a primary alcohol, a hydrogen, or an oxygen, nitrogen, carbon, or sulfur linked to phosphate, a phosphoryl group, a pyrophosphoryl group, or adenosine monophosphate through a phosphodiester or carbon-, nitrogen-, or sulfur-substituted phosphodiester bridge, or to adenosine diphosphate through a phosphodiester or carbon-, nitrogen-, or sulfur-substituted pyrophosphodiester bridge. Also provided are compounds that are the tautomers, pharmaceutically-acceptable salts, esters, and pro-drugs of the inhibitor compounds disclosed herein.

Preferably, A is an N-linked aryl or heterocyclic group, an O-linked aryl or heterocyclic group having the formula —O—Y, or an S-linked aryl or heterocyclic group having the formula -O—Y; both B and C are hydrogen, or either B or C is a halogen, amino, or thiol group and the other of B or C is hydrogen; and D is a primary alcohol or hydrogen. More preferably, A is a nicotinamide group, a pyridyl group, a substituted pyridyl group, a pyrimidyl group, a substituted pyrimidyl group, an O-linked phenyl group, an O-linked substituted phenyl group, an O-linked pyridyl group, an O-linked substituted pyridyl group, an O-linked pyrimidyl group, an S-linked phenyl group, an S-linked substituted phenyl group, an S-linked pyridyl group, an S-linked substituted pyridyl group, or an S-linked pyrimidyl group; both B and C are hydrogen, or either B or C is a halogen, amino, or thiol group and the other of B or C is hydrogen; and D is a primary alcohol or hydrogen. Examples of the inhibitor compounds of the present invention are set out in Table 1.

Particularly preferred are nicotinamide 2'-deoxyribosides. Most preferred are the compounds β-1'-nicotinamide-2'-deoxyribose, β-D-1'-nicotinamide-2'-deoxyribofuranoside, β-1'-pyridyl-2'-deoxyribose, and 5'-phospho-1'-pyridyl-deoxyribose, their tautomers, and their pharmaceutically-acceptable salts.

The compounds of the present invention are useful both in free form and in the form of salts. The term "pharmaceutically acceptable salts" is intended to apply to non-toxic salts derived from inorganic or organic acids and includes, for example, salts derived from the following acids: hydrochloric, sulfuric, phosphoric, acetic, lactic, fumaric, succinic, tartaric, gluconic, citric, methanesulfonic, and p-toluenesulfonic acids.

The compounds of the present invention are potent mechanism-based inhibitors of ADP-ribosyl cyclases, ADP-ribosyl hydrolases, and/or ADP-ribosyl transferases. For example, an assay of enzymatic activity of CD38 ten minutes after treatment with a nicotinamide deoxyriboside inhibitor compound (β-1'-nicotinamide-2'-deoxyribose) showed residual enzymatic activity to be less then 5% of the control. The examples below provide further detail of the effectiveness of this inhibitor, and other inhibitor compounds of the present invention.

Inhibitory activity of the compounds, as disclosed herein, can be determined by standard assays known in the art. For example, the enzyme may

TABLE 1

Inhibitors of ADP-ribosyl transferases, ADP-ribosyl cyclases, and ADP-ribosyl hydrolases

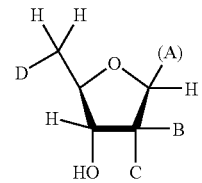

where A = a nitrogen-, oxygen-, or sulfur-linked aryl, alkyl, cyclic, or heterocyclic group, or a group with chemical properties consistent with leaving group function; B and C are hydrogen; and D is a primary alcohol.

TABLE 1-continued

Inhibitors of ADP-ribosyl transferases, ADP-ribosyl cyclases, and ADP-ribosyl hydrolases Examples of A include, but are not limited to, the following:

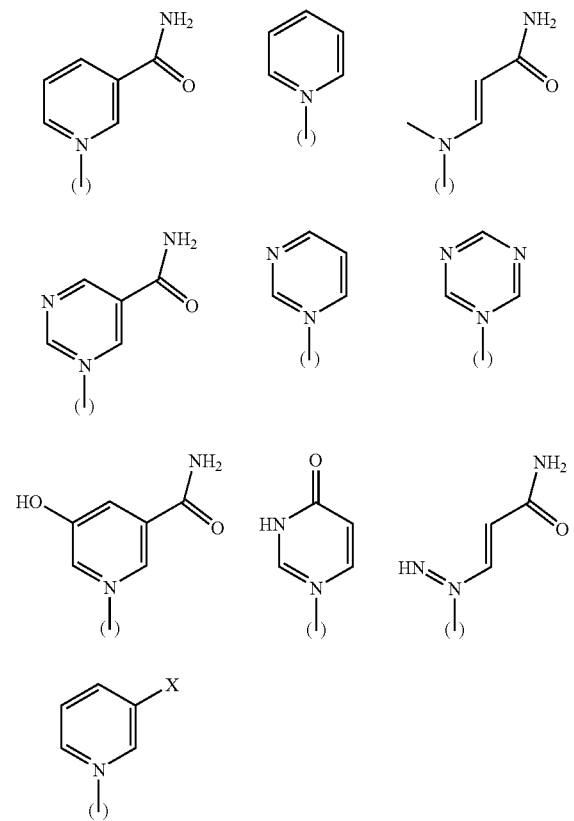

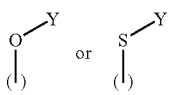

X = halogen, thiol or substituted thiol, amino or substituted amino, oxygen or substituted oxygen, or aryl or alkyl groups or heterocycles or

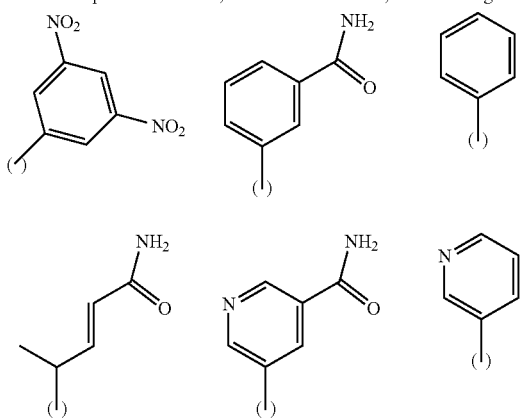

where Y = any group consistent with leaving group function.
Examples of Y include, but are not limited to, the following:

TABLE 1-continued

Inhibitors of ADP-ribosyl transferases, ADP-ribosyl cyclases, and ADP-ribosyl hydrolases

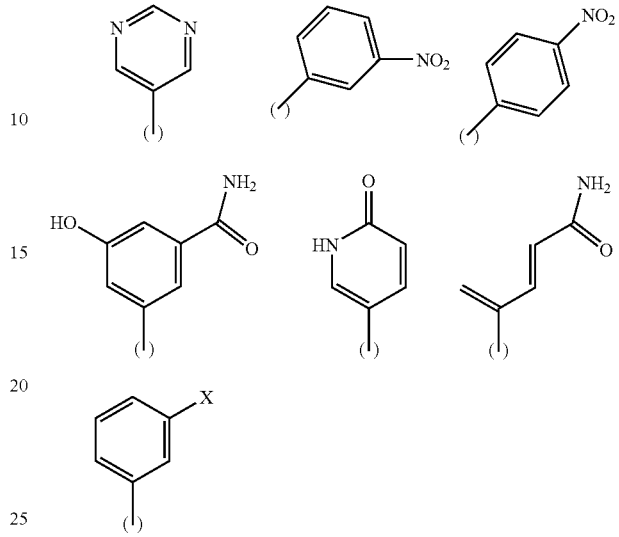

X = halogen, thiol or substituted thiol, amino or substituted amino, oxygen or substituted oxygen, or aryl or alkyl groups or heterocycles In addition, either B or C may be halogen, amino, or thiol group when the other of B or C is a hydrogen. Furthermore, D may be a hydrogen or an oxygen, nitrogen, carbon, or sulfur linked to phosphate, a phosphoryl group, a pyrophosphoryl group, or adenosine monophosphate through a phosphodiester or carbon-, nitrogen-, or sulfur-substituted phosphodiester bridge, or to adenosine diphosphate through a phosphodiester or carbon-, nitrogen-, or sulfur-substituted pyrophosphodiester bridge.

Analogues of adenosine monophosphate or adenosine diphosphate also can replace the adenosine monophosphate or adenosine diphosphate groups.

be incubated with the inhibitor and a substrate of the enzyme, and absorbance then may be monitored, as described below. Additionally, the enzyme may be incubated with a radioactive inhibitor, and radiochemical measurements of reaction rates may be taken, as described below. Slow-onset inhibitor binding may be determined using methods such as those described (32).

Molecules of the novel class of mechanism-based inhibitors disclosed herein accomplish mechanism-based trapping at the catalytic site of their target enzymes. The inhibitor is designed to react rapidly to form a covalent intermediate that cannot cyclize and that is stable to hydrolysis, thereby trapping the enzyme in a catalytically-inactive form. For example, the novel inhibitor β-D-1'-nicotinamide-2'-deoxyribofuranoside acts as a reversible competitive inhibitor ($K_i=1.0$ μM) of CD38, and is followed by slow-onset inactivation of the enzyme. Inactivated enzyme is covalently modified by the deoxyribofuranoside. Active CD38 is slowly regenerated by hydrolysis in the absence of added substrates, and is rapidly regenerated in the presence of excess nicotinamide. These properties of inhibitor action give rise to an effective inhibition constant of 2.9 nM. This novel class of mechanism based inhibitors has potential for the regulation of cyclic ADP-ribose levels through CD38, and provides new tools for investigating the various pathways in which ADP-ribosyl transferases, cyclases, and hydrolases have been implicated.

The biological availability of a compound of formula (I) can be enhanced by conversion into a pro-drug form. Such a pro-drug can have improved lipophilicity relative to the compound of formula (I), and this can result in enhanced membrane permeability. One particularly useful form of pro-drug is an ester derivative. Its utility relies upon the action of one or more of the ubiquitous intracellular lipases to catalyse the hydrolysis of ester groups, to release the compound of formula (I) at or near its site of action. In one form of pro-drug, one or more hydroxy groups in a compound of formula (I) can be O-acylated, to make an acylate derivative.

Pro-drug forms of a 5-phosphate ester derivative of compounds of formula (I) can also be made. These may be particularly useful, since the anionic nature of the 5-phosphate may limit its ability to cross cellular membranes. Conveniently, such a 5-phosphate derivative can be converted to an uncharged bis(acyloxymethyl) ester derivative. The utility of such a pro-drug relies upon the action of one or more of the ubiquitous intracellular lipases to catalyse the hydrolysis of ester groups, releasing a molecule of formaldehyde and the compound of formula (I) at or near its site of action. Specific examples of the utility of, and general methods for making, such acyloxymethyl ester pro-drug forms of phosphorylated carbohydrate derivatives have been described (28-31).

According to another aspect of the present invention, there is provided a method for inhibiting an ADP-ribosyl transferase, ADP-ribosyl cyclase, or ADP-ribosyl hydrolase enzyme. As used herein, "ADP-ribosyl transferase" refers to those enzymes which catalyze the transfer of ADP-ribose (adenosine 5"-diphospho-5'-α-D-ribose) from $NAD^+$ (nicotinamide adenine dinucleotide) to acceptor groups that are chemically reactive as nucleophiles, as well as enzymes that share catalytic site homology with such enzymes. The acceptor groups include the nucleophilic groups of proteins, nucleic acids, sugars, and lipids. Biologically reactive nucleophiles also include other metabolites containing carboxyl groups, amino groups, guanidinium groups, thiol groups, and nitrogens of aromatic or aliphatic compounds, as well as other groups chemically recognized as having nucleophilic character. The ADP-ribosyl transferase family of enzymes produces ADP-ribosylated proteins, ADP-ribosylated nucleic acids, ADP-ribosylated sugars, sugar polymers in homo- or hetero-polymeric forms, glycoproteins, ADP-ribosylated lipids, and ADP-ribosylated compounds of cellular metabolism. Compounds of cellular metabolism include carboxylic acids, sugars, amino acids, lipids, nucleotides, nucleosides, vitamins, and intermediates in the biochemical pathways that synthesize these compounds of cellular metabolism.

As used herein, "ADP-ribosyl cyclase" includes those enzymes that catalyze the conversion of $NAD^+$ to ADP-ribose (adenosine 5"-diphospho-5'-α-D-ribose), in which reaction a chemical bond between carbon 1' of the α-D-ribose group of $NAD^+$ (nicotinamide adenine dinucleotide) is transferred to any nucleophilic acceptor group within the same ADP-ribose molecule, thereby forming a cyclic ring system not existing in the parent molecule of $NAD^+$. Also included are enzymes that share catalytic site homology with such ADP-ribosyl cyclase enzymes. Nucleophilic acceptor groups include nitrogen and oxygen groups of the parent $NAD^+$ molecule (e.g., the structure of cyclic-ADP-ribose, in which the carbon 1' of the α-D-ribose group of $NAD^+$ is cyclized to nitrogen 1' of the adenine ring to form a new cyclic ring).

Additionally, as used herein, "ADP-ribosyl hydrolase" refers to those enzymes that catalyze the transfer of ADP-ribose (adenosine 5"-diphospho-5'-α-D-ribose) from $NAD^+$ (nicotinamide adenine dinucleotide) in the formation of ADP-ribose or cyclic-ADP-ribose. "ADP-ribosyl hydrolase", as used herein, also includes enzymes that catalyze the removal of ADP-ribose, in a hydrolytic reaction, from the ADP-ribosylated groups that are chemically reactive as nucleophiles, defined above. Also included are enzymes that share catalytic site homology with such ADP-ribosyl hydrolase enzymes. ADP-ribosylated groups that are chemically reactive as nucleophiles include the groups of ADP-ribosylated-proteins, ADP-ribosylated-nucleic acids, ADP-ribosylated-sugars, and ADP-ribosylated-lipids from the covalent ADP-ribose. Biologically reactive groups removed from ADP-ribose by hydrolysis may also include biological metabolites containing ADP-ribosylated-carboxyl groups, ADP-ribosylated-amino groups, ADP-ribosylated-guanidinium groups, ADP-ribosylated-thiol groups, ADP-ribosylated-nitrogens of aromatic or aliphatic compounds, and other ADP-ribosylated groups chemically recognized as having nucleophilic character. This family of hydrolases regenerates proteins from ADP-ribosylated proteins, nucleic acids from ADP-ribosylated nucleic acids, sugars from ADP-ribosylated sugars, sugar polymers in homo- or hetero-polymeric forms from their ADP-ribosylated states, and glycoproteins from ADP-ribosylated glycoproteins, lipids from ADP-ribosylated lipids, and removes ADP-ribose from ADP-ribosylated compounds of cellular metabolism. Compounds of cellular metabolism include carboxylic acids, sugars, amino acids, lipids, nucleotides, nucleosides, vitamins, and intermediates in the biochemical pathways that synthesize these biological metabolites.

Examples of ADP-ribosyl transferases, cyclases, and hydrolases include, without limitation, ADP-ribosyl transferases involved in the regulation of gene expression (e.g., SIR family enzymes and their homologues), human CD38, the human ADP-ribosyl cyclase, invertebrate and plant ADP-ribosyl cyclases (e.g., *Aplysia californica* ADP ribosyl-cyclase), and human bone stromal cell antigen (humBST1). Preferably, the enzyme of the present invention is CD38.

The method of the present invention comprises contacting an ADP-ribosyl transferase, ADP-ribosyl cyclase, or ADP-ribosyl hydrolase enzyme with one of the inhibitor compounds of the present invention or their pharmaceutically-acceptable salts, as disclosed herein, in an amount effective to inhibit the enzyme. The ADP-ribosyl transferase, ADP-ribosyl cyclase, or ADP-ribosyl hydrolase enzyme may include any of those described above (e.g., ADP-ribosyl transferases involved in the regulation of gene expression (e.g., SIR family enzymes and their homologues), human CD38, the human ADP-ribosyl cyclase, invertebrate and plant ADP-ribosyl cyclases (e.g., *Aplysia californica* ADP ribosyl-cyclase), and human bone stromal cell antigen (humBST1)). In one embodiment of the present invention, the enzyme is CD38. Moreover, the inhibitor compound may be chosen from any of those disclosed herein. Preferably, the pharmaceutical composition comprises an inhibitor compound chosen from the preferred compounds of the first aspect of the invention. More preferably, the inhibitor compound is chosen from the more preferred compounds of the first aspect of the invention. Most preferably, the inhibitor compound is β-1'-nicotinamide-2'-deoxyribose, β-D-1'-nicotinamide-2'-deoxyribofuranoside, β-1'-pyridyl-2'-deoxyribose, and 5'-phospho-1'-pyridyl-deoxyribose.

As used herein, an "amount effective to inhibit the enzyme" refers to an amount that disables, disrupts, or inactivates the function of the enzyme. Inhibitor compounds contemplated for the inhibition of ADP-ribosyl transferase, ADP-ribosyl cyclase, or ADP-ribosyl hydrolase enzymes may form a combination of enzyme and inhibitor, thereby generating complexes that reduce the catalytic function of the enzyme.

The inhibitor compound of the present invention, or a pharmaceutically-acceptable salt thereof, may be contacted with the enzyme either in vivo or in vitro, using techniques well known to one of skill in the art. Where contacting is effected in vitro, the inhibitor compound may be used as tools for investigating the pathways in which ADP-ribosyl transferase, ADP-ribosyl cyclase, or ADP-ribosyl hydrolase enzymes are involved. Where contacting is effected in vivo, the inhibitor compound may be used to treat a disease or condition in which it is desirable to decrease the activity of an ADP-ribosyl transferase, ADP-ribosyl cyclase, or ADP-ribosyl hydrolase enzyme.

Accordingly, the present invention further provides a method for treating a disease or condition that is directly or indirectly associated with an ADP-ribosyl transferase, ADP-ribosyl cyclase, or ADP-ribosyl hydrolase enzyme in a subject in need of treatment thereof. The method of the present invention comprises administering to the subject any one of the inhibitor compounds of the present invention, or a pharmaceutically-acceptable salt thereof, in an amount effective to treat the disease or condition. As used herein, a "subject" is a mammal, including, without limitation, a cow, dog, human, monkey, mouse, pig, or rat, as described above. Preferably, the subject is a human. The ADP-ribosyl transferase, ADP-ribosyl cyclase, or ADP-ribosyl hydrolase enzyme may include any of those described above (e.g., ADP-ribosyl transferases involved in the regulation of gene expression (e.g., SIR family enzymes and their homologues), human CD38, the human ADP-ribosyl cyclase, invertebrate and plant ADP-ribosyl cyclases (e.g., *Aplysia californica* ADP ribosyl-cyclase), and human bone stromal cell antigen (humBST1)). In one embodiment of the present invention, the enzyme is CD38.

As used herein, "disease" refers to any deviation from, or interruption of, the normal structure or function of any part, organ, or system (or combination thereof) of the body that presents an abnormal or pathologic body state. As further used herein, "condition" refers to any state of physical or mental abnormality. Furthermore, as used herein, "a disease or condition associated with an ADP-ribosyl transferase, ADP-ribosyl cyclase, or ADP-ribosyl hydrolase enzyme" includes a disease or condition wherein an ADP-ribosyl transferase, ADP-ribosyl cyclase, or ADP-ribosyl hydrolase enzyme contributes to (either directly or indirectly), or is responsible for, the pathophysiology of the disease or condition, or in which it is desirable to decrease the activity of an ADP-ribosyl transferase, ADP-ribosyl cyclase, or ADP-ribosyl hydrolase enzyme, or in which it is desirable to regulate the level of cADPR.

Inhibition of cADPR-stimulated calcium release is expected to have significant effects on calcium-mediated signaling pathways in many cells and tissues. Accordingly, in the method of the present invention, the disease or condition associated with an ADP-ribosyl transferase, ADP-ribosyl cyclase, or ADP-ribosyl hydrolase enzyme may include any disease or condition associated with a defect or deficiency in the transmembrane flux of calcium ($Ca^{2+}$) ions into or out of cells, particularly vascular smooth muscle cells, cardiac muscle cells, and cells of the nervous system. Examples of such diseases may include, without limitation, angina (e.g., angina pectoris, chronic stable angina, and vasospastic angina), arrhythmias, atrial fibrillation, hypertension, paroxysmal supraventricular tachycardia, acute disseminated encephalomyelitis (ADEM), acute transverse myelitis, acute viral encephalitis, adrenoleukodystrophy (ALD), adrenomyeloneuropathy, AIDS-vacuolar myelopathy, experimental autoimmune encephalomyelitis (EAE), experimental autoimmune neuritis (EAN), HTLV-associated myelopathy, Leber's hereditary optic atrophy, multiple sclerosis (MS), progressive multifocal leukoencephalopathy (PML), subacute sclerosing panencephalitis, and tropical spastic paraparesis.

In mammals, CD38 and cADPR have been implicated in the regulation of cellular processes, including insulin release (9), lymphocyte activation (2, 10), bone homeostasis (45), and synaptic plasticity (6). Accordingly, the disease or condition associated with an ADP-ribosyl transferase, ADP-ribosyl cyclase, or ADP-ribosyl hydrolase enzyme also may include diseases or conditions associated with insulin release (e.g., diabetes), lymphocyte activation, bone homeostasis, and synaptic plasticity.

In the method of the present invention, the inhibitor compound may be chosen from any of those disclosed herein. Preferably, the inhibitor compound is chosen from the preferred compounds of the first aspect of the invention. More preferably, the inhibitor compound is chosen from the more preferred compounds of the first aspect of the invention. Most preferably, the inhibitor compound is β-1'-nicotinamide-2'-deoxyribose, β-D-1'-nicotinamide-2'-deoxyribofuranoside, β-1'-pyridyl-2'-deoxyribose, and 5'-phospho-1'-pyridyl-deoxyribose.

In the method of the present invention, an inhibitor compound, as disclosed herein, is administered to a subject who has a disease or condition associated with an ADP-ribosyl transferase, ADP-ribosyl cyclase, or ADP-ribosyl hydrolase enzyme, in an amount effective to treat the disease or condition in the subject. As used herein, the phrase "effective to treat the disease or condition" means effective to ameliorate or minimize the clinical impairment or symptoms resulting from the disease or condition associated with an ADP-ribosyl transferase, ADP-ribosyl cyclase, or ADP-ribosyl hydrolase enzyme. For example, where the disease or condition is hypertension, the clinical impairment or symptoms of the disease or condition may be ameliorated or minimized by decreasing systolic and/or diastolic blood pressure, and thereby minimizing dizziness, flushed face, fatigue, headache, epistaxis, nervousness, and other symptoms associated with hypertension, particularly severe hypertension. The amount of inhibitor compound effective to treat a disease or condition associated with an ADP-ribosyl transferase, ADP-ribosyl cyclase, or ADP-ribosyl hydrolase enzyme in a subject in need of treatment thereof will vary depending on the particular factors of each case, including the type of disease or condition associated with an ADP-ribosyl transferase, ADP-ribosyl cyclase, or ADP-ribosyl hydrolase enzyme, the subject's weight, the severity of the subject's condition, and the method of administration. Typically, the dosage for an adult human will range from less than 1 mg to 1000 mg (preferably, 0.1 mg to 100 mg). Nevertheless, requisite amounts can be readily determined by the skilled artisan.

It is within the confines of the present invention that the inhibitor compounds disclosed herein may be administered to a subject who is already receiving an inhibitor of the ryanodine receptor or an antagonist that binds the ryanodine receptor. The inhibitor compounds of the present invention, when contacted with the ADP-ribosyl transferase, cyclase, and hydrolase enzymes described herein, result in a decrease in cADPR concentration. It is expected that this decrease would prevent cADPR from competing against antagonists or inhibitors binding at the same site on the ryanodine receptors.

In accordance with the method of the present invention, the inhibitor compound may be administered to a human or animal subject by known procedures, including, without limitation, oral administration, parenteral administration (e.g., epifascial, intracapsular, intracutaneous, intradermal, intramuscular, intraorbital, intraperitoneal, intraspinal, intrasternal, intravascular, intravenous, parenchymatous, or subcutaneous administration), transdermal administration, and administration by osmotic pump. Preferably, the inhibitor compound of the present invention is administered orally.

For oral administration, the inhibitor compound may be formulated in solid or liquid preparations, e.g., capsules, tablets, powders, granules, dispersions, solutions, and suspensions. Such preparations are well known in the art as are other oral dosage forms not listed here. In a preferred embodiment, the inhibitor compounds of the invention are tableted with conventional tablet bases, such as lactose, sucrose, mannitol, and corn starch, together with a binder, a disintegration agent, and a lubricant. These exipients are well known in the art. The formulation may be presented with binders, such as crystalline cellulose, cellulose derivatives, acacia, corn starch, or gelatins. Additionally, the formulation may be presented with disintegrators, such as corn starch, potato starch, or sodium carboxymethylcellulose. The formulation also may be presented with dibasic calcium phosphate anhydrous or sodium starch glycolate. Finally, the formulation may be presented with lubricants, such as talc or magnesium stearate. Other components, such as coloring agents and flavoring agents, also may be included. Liquid forms for use in the invention include carriers, such as water and ethanol, with or without other agents, such as a pharmaceutically-acceptable surfactant or suspending agent.

For parenteral administration (i.e., administration by injection through a route other than the alimentary canal), the inhibitor compound may be combined with a sterile aqueous solution which is preferably isotonic with the blood of the subject. Such a formulation may be prepared by dissolving a solid active ingredient in water containing physiologically-compatible substances, such as sodium chloride, glycine, and the like, and having a buffered pH compatible with physiological conditions, so as to produce an aqueous solution, then rendering said solution sterile. The formulations may be presented in unit or multi-dose containers, such as sealed ampules or vials. The formulation may be delivered by any mode of injection, including, without limitation, epifascial, intracapsular, intracutaneous, intradermal, intramuscular, intraorbital, intraperitoneal, intraspinal, intrasternal, intravascular, intravenous, parenchymatous, or subcutaneous.

For transdermal administration, the inhibitor compound may be combined with skin penetration enhancers, such as propylene glycol, polyethylene glycol, isopropanol, ethanol, oleic acid, N-methylpyrrolidone, and the like, which increase the permeability of the skin to the inhibitor compound, and permit the inhibitor compound to penetrate through the skin and into the bloodstream. The inhibitor compound/enhancer composition also may be further combined with a polymeric substance, such as ethylcellulose, hydroxypropyl cellulose, ethylene/vinylacetate, polyvinyl pyrrolidone, and the like, to provide the composition in gel form, which may be dissolved in solvent, such as methylene chloride, evaporated to the desired viscosity, and then applied to backing material to provide a patch. The inhibitor compound may be administered transdermally, at or near the site on the subject where the disease or condition is localized. Alternatively, the inhibitor compound may be administered transdermally at a site other than the affected area, in order to achieve systemic administration.

The inhibitor compound of the present invention also may be released or delivered from an osmotic mini-pump or other time-release device. The release rate from an elementary osmotic mini-pump may be modulated with a microporous, fast-response gel disposed in the release orifice. An osmotic mini-pump would be useful for controlling release, or targeting delivery, of the inhibitor compound.

In another aspect, the present invention provides a pharmaceutical composition, comprising a pharmaceutically effective amount of an inhibitor compound of the first aspect of the invention. The inhibitor compound may be chosen from any of those described above. Preferably, the pharmaceutical composition comprises an inhibitor compound chosen from the preferred compounds of the first aspect of the invention. More preferably, the inhibitor compound is chosen from the more preferred compounds of the first aspect of the invention. Most preferably, the inhibitor compound is β-1'-nicotinamide-2'-deoxyribose, β-D-1'-nicotinamide-2'-deoxyribofuranoside, β-1'-pyridyl-2'-deoxyribose, and 5'-phospho-1'-pyridyl-deoxyribose.

In the pharmaceutical composition of the present invention, the pharmaceutically-acceptable carrier must be "acceptable" in the sense of being compatible with the other ingredients of the composition, and not deleterious to the recipient thereof. Examples of acceptable pharmaceutical carriers include carboxymethyl cellulose, crystalline cellulose, glycerin, gum arabic, lactose, magnesium stearate, methyl cellulose, powders, saline, sodium alginate, sucrose, starch, talc, and water, among others. Formulations of the pharmaceutical composition may be conveniently presented in unit dosage.

The formulations of the present invention may be prepared by methods well-known in the pharmaceutical art. For example, the inhibitor compound may be brought into association with a carrier or diluent, as a suspension or solution. Optionally, one or more accessory ingredients (e.g., buffers, flavoring agents, surface active agents, and the like) also may be added. The choice of carrier will depend upon the route of administration. The pharmaceutical composition would be useful for administering the inhibitor composition of the present invention to a subject to treat a disease or condition associated with an ADP-ribosyl transferase, ADP-ribosyl cyclase, or ADP-ribosyl hydrolase enzyme, including any of those described above. The inhibitor compound is provided in an amount that is effective to treat a disease or condition associated with an ADP-ribosyl transferase, ADP-ribosyl cyclase, or ADP-ribosyl hydrolase enzyme in the subject. That amount may be readily determined by the skilled artisan, as described above.

In another aspect, the present invention provides a method of preparing the inhibitor compounds of the first aspect of the invention. The method may include one or more of the methods disclosed herein, as well as other methods that will be apparent to those of skill in the art. The method of preparing the inhibitor compounds of the present invention may involve a reaction in the presence of silver, as an adaptation of several $Hg^{2+}$ couplings and chlorosugars to form nucleosides. In general, the method will comprise the following steps: (a) contacting a deoxyribose sugar (e.g., β-3,5-bis-parachlorobenzoyl-1-pyridyl-2-deoxyribose), or a mixture containing a deoxyribose sugar and a base (e.g., 3,5-bis-parachlorobenzoyl-1-α-chloro-2-deoxyribose and nicotinamide), with a mixture containing both a silver compound (e.g., $AgSbF_6$) and the compound to be reacted with the deoxyribose sugar (e.g., pyridine or nicotinamide), thereby forming a reaction mixture; (b) redissolving the reaction mixture in MeOH; (c) adding $NH_4Cl$ to the reaction mixture; (d) filtering the reaction mixture to remove precipitated residual silver; (e) treating the reaction mixture with $NH_3$ in MeOH; (f) adding water to the reaction mixture; and (g) purifying the reaction mixture (e.g., with HPLC).

For example, β-nicotinamide-2'-deoxyribose (βNdR) may be synthesized using the following general procedure: 3,5-bis-parachlorobenzoyl-1-α-chloro-2-deoxyribose (16) may be added to nicotinamide in one flask. In a second flask, nicotinamide may be added to $AgSbF_6$ and acetonitrile. The homogeneous silver solution may be cooled with ice, added to the flask containing the base and sugar, then stirred while chilling in an ice/salt bath. The reaction then may be warmed to room temperature, and stirred. The reaction mixture then may be evaporated, and the residue redissolved in MeOH. Residual silver may be precipitated by addition of $NH_4Cl$, and a further amount of $NH_4Cl$ may be added to precipitated residual silver. The mixture may be filtered (e.g., through Celite™) to remove AgCl, and the filtrate then may be evaporated. NMR then may be used on the isolated material to determine the percent yield and the proportions of α- and β-3,5-bis-p-chlorobenzoyl-1-nicotinamide-2-deoxyribose stereoisomers in the mixture. The protected nicotinamide deoxyriboses (α and β) then may be subjected to deprotection, without further purification, by treatment with $NH_3$ in MeOH. The MeOH and $NH_3$ may be evaporated, and the subsequent residue may be redissolved in methanol. Addition of water may result in the precipitation of organic material, which may be removed by centrifugation. The aqueous phase may be purified by HPLC to yield the pure α and β deprotected isomers. These isomers may be analyzed by $^1H$ NMR, after evaporation and solubilization in $D_2O$.

Similarly, β-1'-pyridyl-2'-deoxyribose may be synthesized by the following general method: β-3,5-bis-parachlorobenzoyl-1-pyridyl-2-deoxyribose may be added to one flask. To a second flask may be added pyridine, $AgSbF_6$, and $CH_2Cl_2$. The silver solution may be cooled, and then added to the flask containing the base and sugar. The solution may be stirred in an ice/salt bath, until a gray precipitate forms. The reaction mixture then may be warmed to room temperature, and further stirred. The reaction mixture may be evaporated, and the residue redissolved in MeOH. $NH_4Cl$ then may be added to the precipitated residual silver. The mixture may be filtered (e.g., through Celite™), and then evaporated. NMR may be used to determine the percent yield and the proportion represented by each stereoisomer (β and α) in the mixture. The protected material above may be subjected to deprotection without further purification by treatment with $NH_3$ in MeOH. The MeOH and $NH_3$ may be evaporated, and the residue suspended in methanol. Addition of water may result in the precipitation of organic material, which may be removed by centrifugation. The aqueous phase may be purified by HPLC to yield the pure α and β deprotected isomers. These isomers may be analyzed by $^1H$ NMR following rapid evaporation and solution in $D_2O$.

The present invention is described in the following Experimental Details section, which is set forth to aid in the understanding of the invention, and should not be construed to limit in any way the scope of the invention as defined in the claims which follow thereafter.

EXPERIMENTAL DETAILS

1. Introduction

Human CD38 (1,2) and related ADP-ribosyl-cyclases (3,4) are attractive targets for inhibitor design based upon their ability to synthesize cyclic ADP-ribose (cADPR) from $NAD^+$ (5). The compound cADPR is formed by the intramolecular transfer of ADP-ribose of $NAD^+$ to N1 of adenine, with retention of the β-stereochemistry (Scheme 1). The cADPR product binds ryanodine receptors that control $Ca^{2+}$ release (1, 7-10); therefore, it is a putative second messenger for $Ca^{2+}$ release inside cells. The mechanism of cADPR formation, which is catalyzed by ADP-ribosyl cyclases, occurs through decomposition of the $NAD^+$ C1'-N1 bond, resulting in the formation of an ADP-ribosyl electrophile that has been demonstrated to be a covalent intermediate at the active site of the enzyme (11-15). Relying upon this mechanistic description of the enzyme function, the inventors have designed, synthesized, and evaluated a new class of mechanism-based inhibitors for the ADP-ribosyl cyclases. These novel compounds function via a combination of binding and mechanism-based covalent inactivation of the ADP-ribosyl cyclase enzymes. The parent structure, nicotinamide deoxyriboside, is a potent inhibitor of CD38—the human ADP-ribosyl cyclase. The chemical synthesis of 2'-deoxy-β-D-ribofuranosides of nicotinamide, and several analogues, is described herein, as is their inhibitory properties in respect of CD38 catalytic function.

2. Materials and Methods

A. Synthesis of 3,5-bis-p-chlorobenzoyl-1-α-chloro-2-deoxyribose 3,5-bis-p-chlorobenzoyl-1-α-chloro-2-deoxyribose was prepared using the published procedure (16).

B. Expression of Human CD38

The soluble catalytic domain of human CD38 was expressed in yeast using the expression vector CD38S2, according to published procedures (17).

C. Synthesis of β-3,5-bis-p-chlorobenzoyl-1-nicotinamide-2-deoxyribose 100 mg (0.24 mmol) of 3,5-bis-p-chlorobenzoyl-1-α-chloro-2-deoxyribose was added to a flask, along with 90 mg (0.75 mmol) of nicotinamide. To a second flask was added 5 mg of nicotinamide (0.041 mmol), 86 mg of $AgSbF_6$ (0.25 mmol), and 5 ml of acetonitrile. The homogeneous silver solution was cooled to 0° C. with ice, then added to the flask containing the base and sugar. The solution was stirred for 2 h while chilled by an ice/salt bath. The light-gray precipitate that formed was presumed to be AgCl. The reaction then was warmed to room temperature, and stirred an additional 2 h. The reaction mixture was evaporated, and the residue was redissolved in MeOH. Residual silver was precipitated by addition of 1 mg of $NH_4Cl$, and a 1-mg quantity of $NH_4Cl$ was added to precipitated residual silver. The mixture was filtered through Celite™ to remove AgCl, and the filtrate then was evaporated. Using NMR, the isolated material was determined to be a mixture of α- and β-3,5-bis-p-chlorobenzoyl-1-nicotinamide-2-deoxyribose stereoisomers (9:1; β:α), with a yield of 70%. This procedure is an adaptation of several $Hg^{2+}$ couplings and chlorosugars to form nucleosides (18). Selected $^1H$ NMR resonances: $d^4$-MeOH, δ 6.9 d, α 1'H, 6.85, t, β 1'H.

D. Synthesis of β-nicotinamide-2'-deoxyribose (βNdR)

The protected nicotinamide deoxyriboses (α and β) were subjected to deprotection, without further purification, by treatment with 4 ml of 2 M $NH_3$ in MeOH for 12 h at 4° C. At the end of this time, thin-layer chromatography (TLC) indicated consumption of the starting material. The MeOH and $NH_3$ were evaporated at reduced pressure, and the subsequent residue was redissolved in 300 µl of methanol. Addition of 1 ml of water resulted in the precipitation of organic material, which was removed by centrifugation. The aqueous phase was purified by HPLC (1 mM $NH_4AcO$, pH 7.0) to yield the pure α and β deprotected isomers. These isomers were analyzed by $^1$H NMR, after evaporation and solubilization in $D_2O$. The absorbance of inhibitor solutions was measured at 266 nm ($\epsilon$=4600 $M^{-1}$ $cm^{-1}$). Solutions were stored frozen at −78° C. $^1$H NMR (β isomer) $D_2O$: δ 9.6, s, 1H; 9.3 d, 1H; 8.8, t, 1H, 8.5, d 1H; 6.7, t, 1H; 5.3, m, 1H; 4.8, m 1H; 4.4, m 2H; 2.8-3.2 m 2H.

E. Synthesis of β-3,5-bis-p-chlorobenzoyl-1-pyridyl-2-deoxyribose 50 mg (0.12 mmol) of 3,5-bis-p-chlorobenzoyl-1-α-chloro-2-deoxyribose was added to a flask. To a second flask was added 30 mg of pyridine (0.38 mmol), 43 mg of $AgSbF_6$ (0.12 mmol), and 5 ml of $CH_2Cl_2$. The silver solution was cooled to 0° C., and added to the flask containing the base and sugar. The solution was stirred for 2 h in an ice/salt bath. The gray precipitate that was observed was presumed to be AgCl. The reaction mixture then was warmed to room temperature, and stirred for an additional 2 h. The reaction mixture was evaporated, and the residue was redissolved in MeOH. 1 mg of $NH_4Cl$ then was added to the precipitated residual silver. The mixture was filtered through Celite™, and then evaporated. Using NMR, the material was determined to be a mixture of the stereoisomers (11:1, β:α) in a yield of 95%. Selected $^1$H NMR resonances: $d_3$-AcCN, δ 6.85 d, α 1'H, 6.8, t, β 1'H.

F. Synthesis of β-1'-pyridyl-2'-deoxyribose

The protected material above was subjected to deprotection without further purification by treatment with 4 ml of 2 M $NH_3$ in MeOH for 12 h at 4° C. The MeOH and $NH_3$ were evaporated at reduced pressure, and the residue was suspended in 300 μl of methanol. Addition of 1 ml of water resulted in the precipitation of organic material, which was removed by centrifugation. The aqueous phase was purified by HPLC to yield the pure α and β deprotected isomers in a yield of 90%. These isomers were analyzed by $^1$H NMR following rapid evaporation and solution in $D_2O$. $^1$H NMR (β isomer) $D_2O$: δ 9.2, d, 2H; 9.0 t, 2H; 8.5, t, 1H, 6.7, t, 1H; 4.9, m, 1H; 4.6, m 1H; 4.4, m, 2H; 2.8-3.2 m, 2H.

G. Synthesis of 5'-phospho-1'-β-pyridyl-2'-deoxyribose 4 mg of β-pyridyl-deoxyriboside-acetate (0.01 mmol) was dissolved in 500 ml of trimethylphosphate, and the reaction was cooled to −20° C. 15 μl of phosphorus oxychloride (0.1 mmol) were added, and the reaction was continued at this temperature for 78 h. The 5'-phosphorylated compound was purified by HPLC in a yield of 85%, and characterized by MS molecular formula: $C_{10}H_{15}O_6NP$; MS data: $M^+$=276.

H. Activity and Inhibition Measurements (β-1'-nicotinamide-2'-deoxyribose)

Human CD38 (200 nM) was incubated with β-1'-nicotinamide-2'-deoxyribose (5 μM) in a volume of 100 μl of 50 mM potassium phosphate (pH 7.5). Aliquots of the reaction were assayed by placing 5 μl of the reaction mixture into 1 ml of 50 mM HEPES (pH 7.5) containing 100 μM $NGD^+$, at 30, 60, 90, 120, 180, or 300 sec. The conversion of $NGD^+$ to cGDPR was monitored by determining absorbance at 295 nm. A reaction mixture lacking inhibitor was used as a control. Activity was determined as a function of time, and fitted to the equation $A(t)=A_0e^{-kt}$, where $A_0$ is activity at time zero (control), t is time in seconds, and k is the observed pseudo-first-order rate constant.

I. Radiochemical Measurement of Reaction Rates (β-1'-nicotinamide-2'-deoxyribose)

[2'-$^3$H]β-1'-nicotinamide-2'-deoxyribose ([2'-$^3$H]βNdR) was used to measure the covalent interaction of inhibitor with CD38 as follows: 9 μM inhibitor with specific activity of 1233 cpm/nmol was incubated with 1.2 μM CD38 in a volume of 1 ml of 50 mM potassium phosphate (pH 7.5). The reactions were started by enzyme addition, and quenched by freezing in a dry ice/acetone bath after 30, 60, 90, 120, 250, 500, and 1000 sec. Samples were placed on 1 ml gel filtration columns (0° C.) that were used to separate protein from free inhibitor. Columns were cooled on ice, and eluted with cold (0° C.) 10 mM potassium phosphate (pH 7.5) as eluant. Fractions (1 ml) were combined with 9 ml of scintillation fluid, and counted for radioactivity. A sample lacking enzyme, but having the same incubations, was performed as a blank control. A sample using the α-[2'-$^3$H]nicotinamide-2'-deoxyribose of equal concentration and specific activity, and having the same incubations, was performed as a second control. The observed cpm in the protein peak (fractions 3+4) was fitted to the equation $A(t)=A_0(1-\exp(-kt))+B$, where A(t) is the cpm in protein at time t, $A_0$ is the cpm at reaction completion, k is the observed pseudo-first-order rate constant, B is the activity of the blank, and t is the time in seconds.

J. Activity and Inhibition Measurements (β-1'-pyridyl-2'-deoxyribose)

Human CD38 (200 nM) was incubated with β-1'-pyridyl-2'-deoxyribose (25 mM) in a volume of 100 μl of 50 mM Tricine (pH 7.5). Aliquots of the reaction (5 μl) were assayed by placing into 1 ml of 50 mM HEPES (pH 7.5) containing 100 μM $NGD^+$ at 750, 1500, 2250, 3000, 4000, 8000, and 14400 s. The conversion of $NGD^+$ to cGDPR was monitored by absorbance at 295 nm. A reaction mixture lacking inhibitor was used as a control. Activity was determined as a function of time, and fitted to the equation $A(t)=C+A_0e^{-kt}$, where $A_0$ is activity at time zero (control), t is time in s, k is the observed pseudo-first-order rate constant, and C represents uninhibited activity at equilibrium.

K. Radiochemical Measurement of Reaction Rates (β-1'-pyridyl-2'-deoxyribose)

The covalent interaction of [2'-$^3$H]β-1'-pyridyl-2'-deoxyribose with CD38 was measured as follows: 25 mM inhibitor with specific activity of 1233 cpm/nmol was incubated with 25.2 μM CD38 in a volume of 50 μl of 50 mM Tricine (pH 7.5). The reactions were started by enzyme addition, and quenched by freezing in a dry ice/acetone bath after 2 h, 7200 s. Samples were placed on (0° C.) 1-ml gel filtration columns (P-10) that were used to separate protein from free inhibitor. Columns were cooled on ice, and eluted with cold (0° C.) 10 mM potassium phosphate (pH 7.5) as eluant. Fractions (1 ml) were combined with 9 ml of scintillation fluid, and counted for radioactivity. A sample lacking enzyme, but undergoing the same incubations, was performed as a blank control. A sample using the α-[2'-$^3$H]nicotinamide-2'-deoxyribose of equal concentration and specific activity, and the same incubations, was used as a second control. The observed cpm in the protein peak (fractions 3+4) were fitted to the equation $A(t)=A_0(1-\exp(-kt))+B$, where A(t) is the cpm in protein at time t, $A_0$ is the cpm at reaction completion, k is the observed pseudo-first-order rate constant, B is the activity of the blank, and t is the time in s.

L. Off-Rate Measurement

Recovery of CD38 catalytic activity after inactivation with β-1'-nicotinamide-2'-deoxyribose was measured in reaction mixtures containing 500 nM CD38, 50 mM inhibitor, and 15 μM deoxyriboside. After timed intervals, 5 μl of the reaction mixture were added to a 1-ml reaction of 50 mM HEPES (pH 7.5) containing 300 μM $NGD^+$. A control was also prepared without the inhibitor. Production of cGDPR was determined by monitoring absorbance at 295 nm. The absorbance was fitted to the equation $A(t)=vt+(b-v)(1-\exp(-k_{off}t))/k_{off}+A_0$ (19), where $k_{off}$ is the observed rate constant, b is the initial rate, v is the final rate, and $A_0$ is the initial absorbance.

M. Determination of $K_i$ and $k_{chem}$ by Competitive Method

CD38 was used to start reactions containing 1-ml solutions of 50 mM potassium phosphate, 100 µM NGD, and 50, 25, 12.5, 6.25, and 0 µM βNdR. Reactions were initiated with 2 µl of 7 µM CD38, and reaction progress was monitored by measurement of absorbance at 295 nm. The initial slopes were used to determine the $K_i$ value. The time course of absorbance for each sample was fitted to the equation $A(t) = vt+(b-v)(1-\exp(-kt))/k+A_0$, where k is the observed rate constant, b is the initial rate, v is the final rate, and $A_0$ is the initial absorbance. The rate constant $k_{chem}$ (FIG. 3) was determined as reported (19).

3. Results and Discussion

The reaction mechanism of CD38, and, presumably, the mechanisms of related ADP-cyclase enzymes, involve the formation of a covalent intermediate along the catalytic reaction coordinate (12). Numerous glycotransferases form covalent intermediates during the catalytic cycle. These enzymes have been inhibited by compounds that feature a 2'-fluorine substitution for the 2'-hydroxyl (2'-OH) group (20-23). This strategy has also proved successful for inhibition of CD38 (12, 24, 25). The proposed mechanism of action for these inhibitor compounds is the formation of a reaction intermediate that is resistant to normal hydrolytic breakdown. The intermediate is probably resistant to nucleophilic displacement on the enzyme because of the inductive effect of the fluorine atom (12, 20-23).

The proposed mechanism is supported by increased stability of fluorinated sugars, as compared with their non-fluorinated ribosyl substrates, in acid-catalyzed hydrolysis reactions (26). Nevertheless, the rates for decomposition of fluoro-substituted covalent intermediates are lower than would be predicted from their relative stabilities, as compared with those of normal substrates, based on rate comparisons for these same reactants in solution hydrolysis reactions (26). This comparison suggests that substrate reactivity on the enzyme is uniquely accelerated by the presence of the 2'-OH group in the molecule. One physical explanation for this effect suggests that the 2'-OH plays an integral role in the mediation of proton transfer to the carboxylate nucleophile identified as the intermediate's point of attachment to the enzyme (12). This protonation could assist carboxylate departure at the transition state, and lower transition state energy.

The inventors tested their hypothesis by synthesizing nicotinamide 2'-deoxyribosides (βNdR). These derivatives are intrinsically more reactive in solution hydrolysis reactions than are their ribose cousins. Chemical instability toward hydrolysis implies that the derivatives should react at least as fast as substrate, if chemical stability dominates at the enzyme-catalyzed transition state, but should be effective inhibitors of CD38, if the removal of a 2'-OH group disrupts an essential proton transfer from the 2'-hydroxyl moiety.

Figure 2:
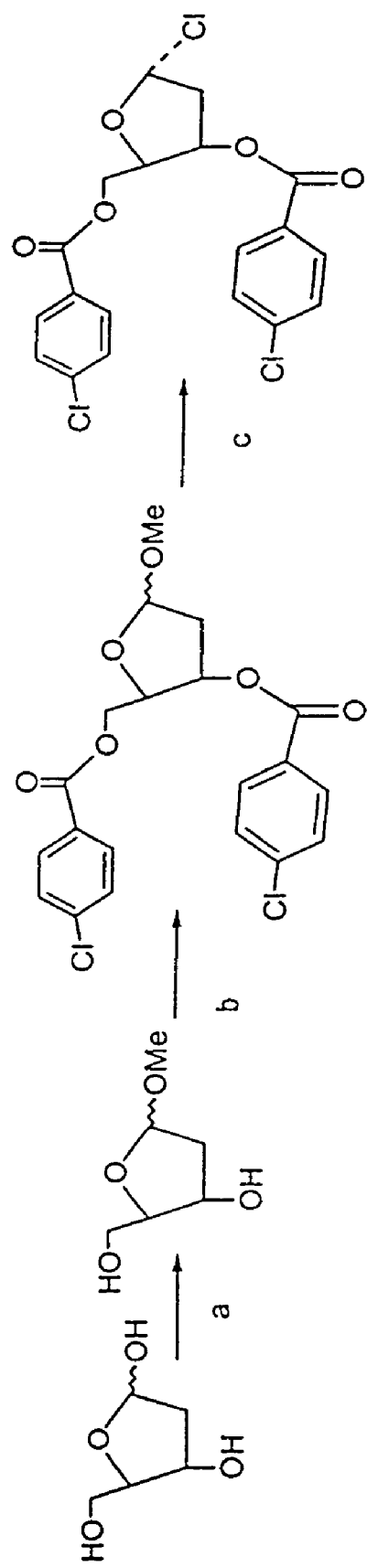
FIG. 2 depicts the synthesis of 3,5-bis-parachlorobenzoyl-α-1-chloro-2-deoxyribose. Conditions: a—HCl, MeOH; b—parachlorobenzoyl chloride, pyridine; c—AcOH, $Et_2O$, HCl, 273 K
Figure 3:
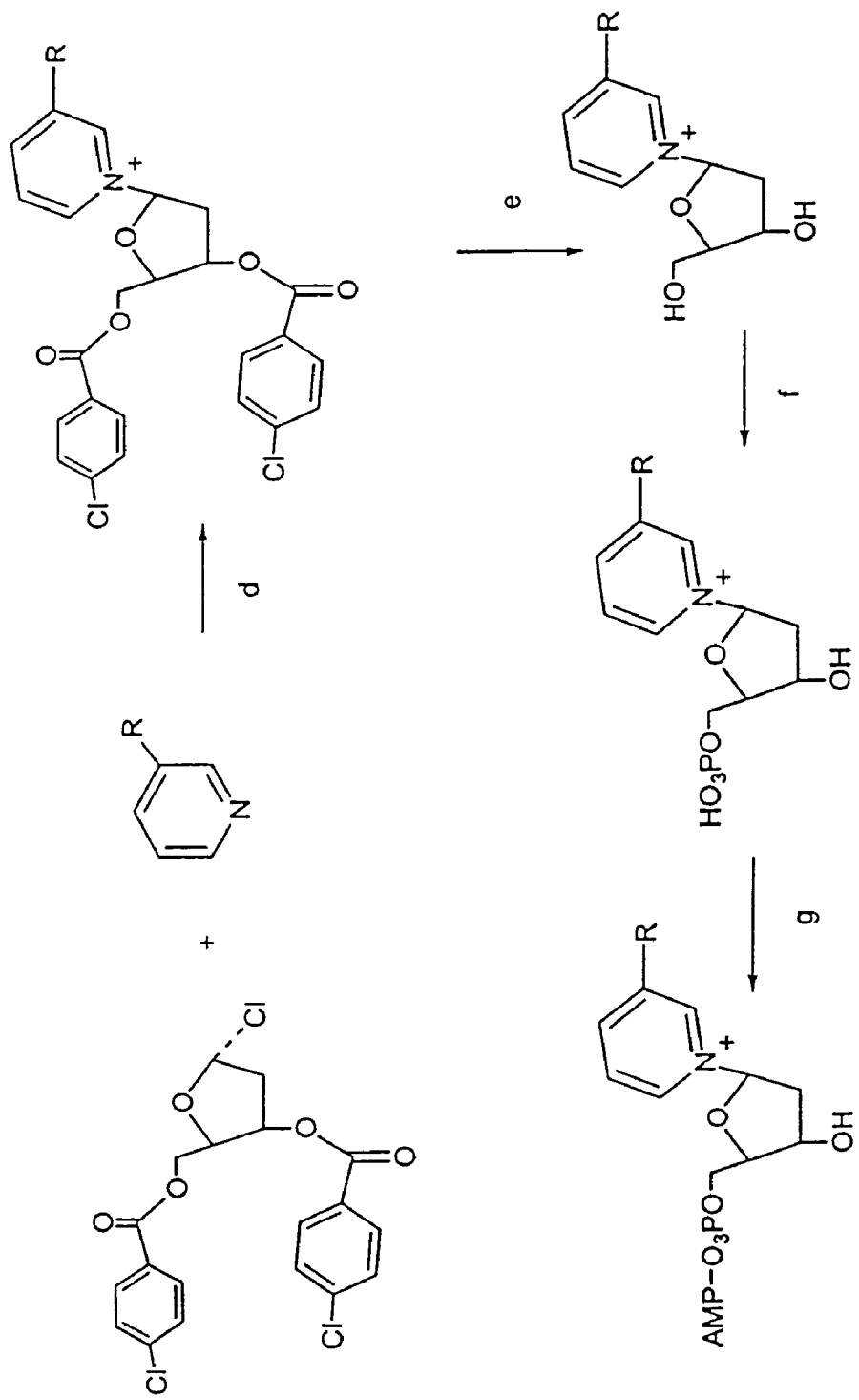
FIG. 3 illustrates the synthesis of pyridyl-substituted derivatives of deoxyribose. R=CONH$_2$; R=H. Conditions: d—1.0 eq. AgSbF$_6$, AcCN, 273 K; e—2 M NH$_3$, MeOH; f—OPCl$_3$, (EtO)$_3$PO; g—1 M N,N-ethyl-3-(-1-dimethyl aminopropyl carbodiimide, 0.5 M HEPES, pH 6.0

Synthesis of βNdR and derivatives is unprecedented from available literature. The inventors' synthetic investigations eventually led to the development of a versatile silver coupling methodology which allowed direct access to either α or β nucleosides in high yield (18). This method provided good yields to permit the synthesis of a variety of pyridyl-substituted deoxy derivatives. The general synthetic routes are shown in FIG. 2 and FIG. 3.

A. Inhibition of CD38 by βNdR

Figure 6:
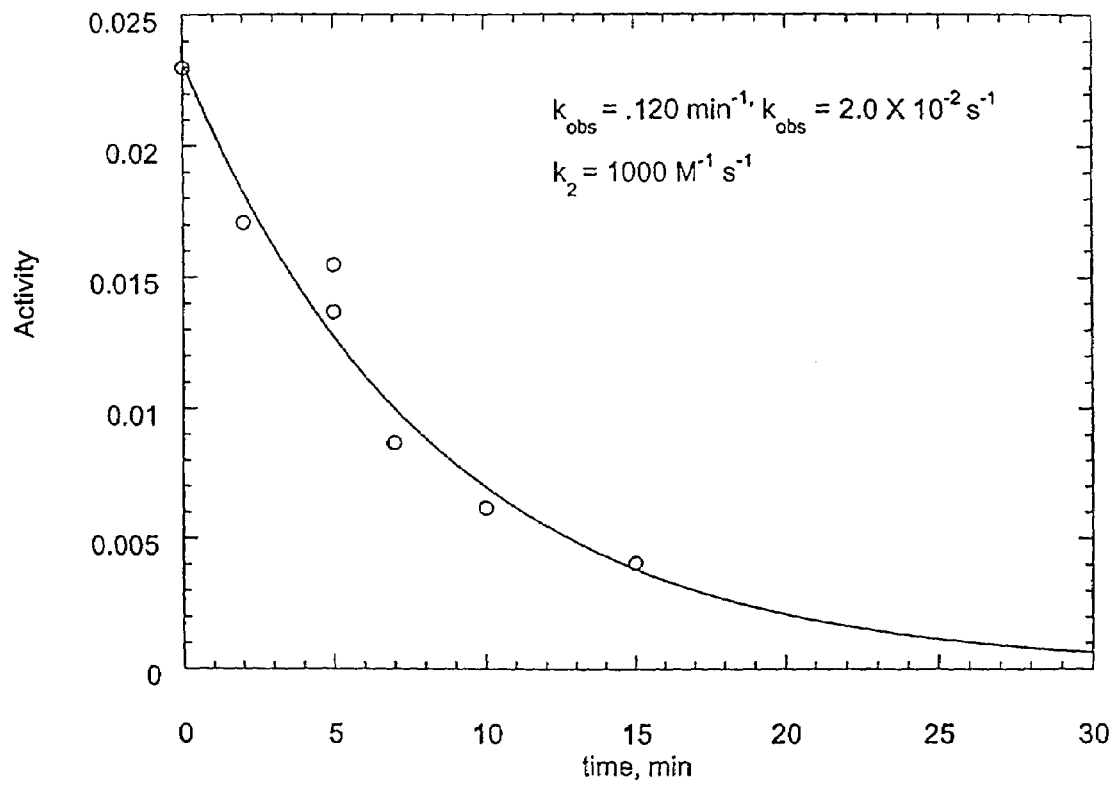
FIG. 6 illustrates the activity of CD38 as measured by the conversion of NGD$^+$ to cGDPR (activity curves not shown). Activities were measured at the times indicated after incubation with nicotinamide-2'-deoxyribose (2 μM). The solid curve represents the best fit to the equation $A(t) = A_0 \exp(-k_{obs}t)$. The value $k_2$, the bimolecular rate constant, is determined by the equality $k_2[I] = k_{obs}$.
Figure 7:
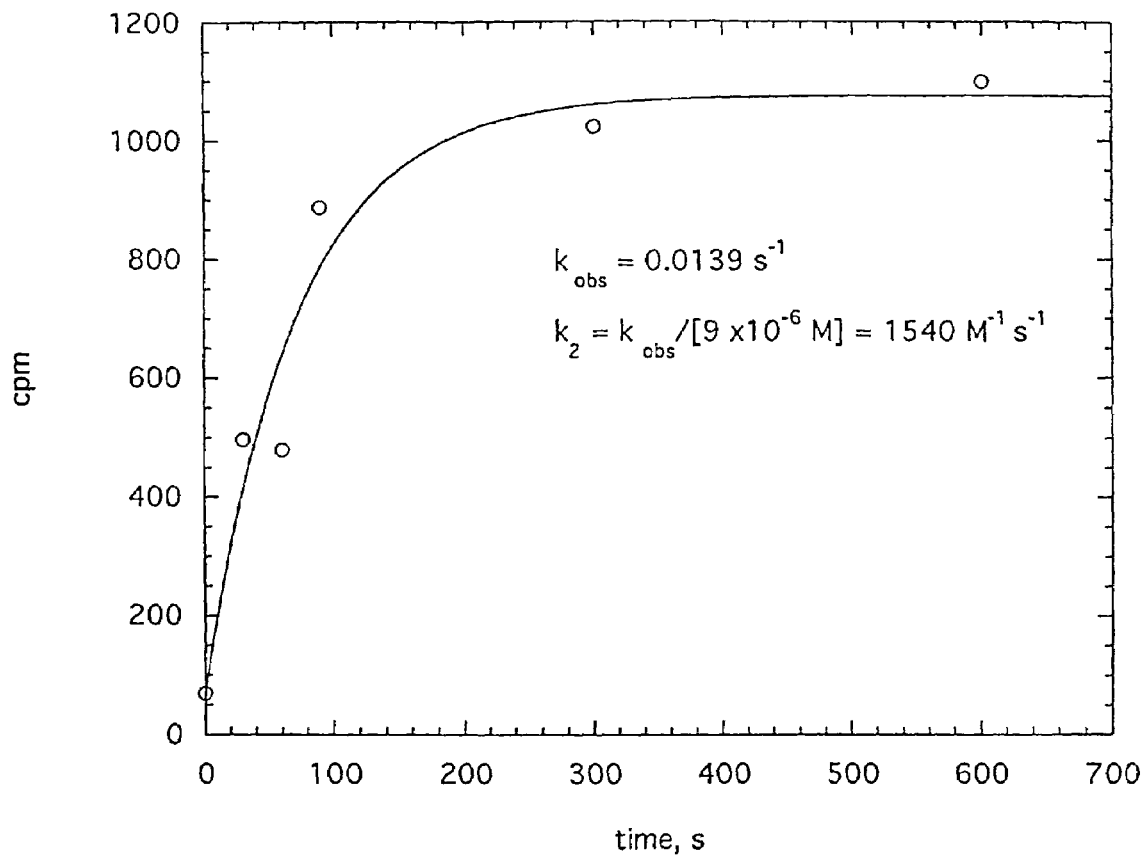
FIG. 7 depicts the radiochemical titration of CD38. CD38 (1.2 μM) was separated from [2'-$^3$H]nicotinamide-2'-deoxyribose (9 μM) by gel-filtration at the indicated times, as described in the Experimental Details section. The solid curve represents the best fit to the equation $A(t) = A_0(1-\exp(-k_{obs}t))$. The value $k_2$, the bimolecular rate constant, is determined by the equality $k_2[I] = k_{obs}$.

Treatment of CD38 with β-1'-nicotinamide-2'-deoxyribose (βNdR) confirmed that the compound rapidly inhibits the enzymatic activity of CD38. Assay of enzymatic activity 10 min after treatment of the enzyme (500 nM) with excess inhibitor (10 µM) showed residual enzymatic activity to be less than 5% of the control. The inactivation rate of CD38 at an inhibitor concentration of 2 µM showed that inactivation follows a pseudo-first-order rate process (FIG. 6), with a bimolecular rate constant ($k_{on}$) of 1100 $M^{-1}$ $sec^{-1}$ at 25° C. This rate constant was confirmed by the use of radiolabeled inhibitor, [2'-$^3$H]βNdR. The binding of this inhibitor to CD38 was determined by scintillation counting after rapid gel filtration was used to separate free inhibitor from its protein complex. This method allowed measurement of $k_{on}$ by an exponential fit of accumulated cpm bound versus time (FIG. 7). The value for $k_{on}$ determined by this method was 1540 $M^{-1}$ $sec^{-1}$.

B. Kinetic Constants for CD38 Inhibition by βNdR

Figure 4:
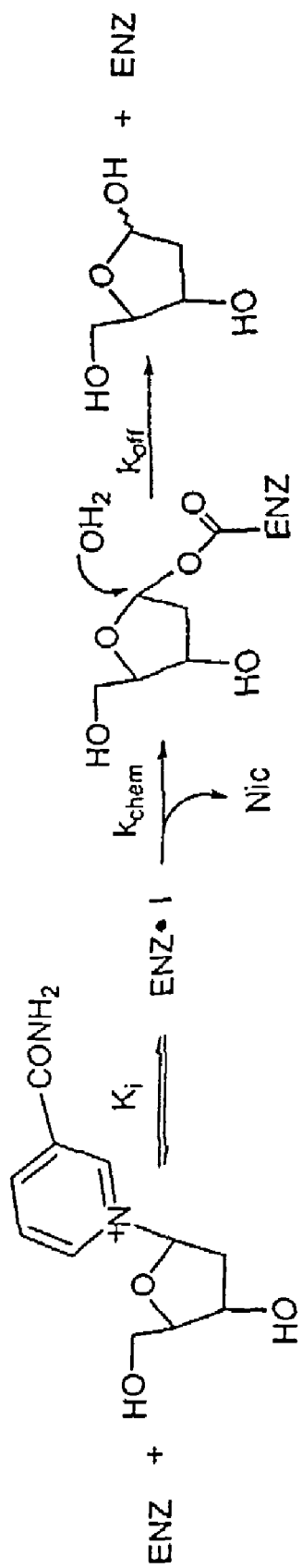
FIG. 4 sets forth the proposed mechanism of inhibition of CD38 by nicotinamide deoxyribose.
Figure 8:
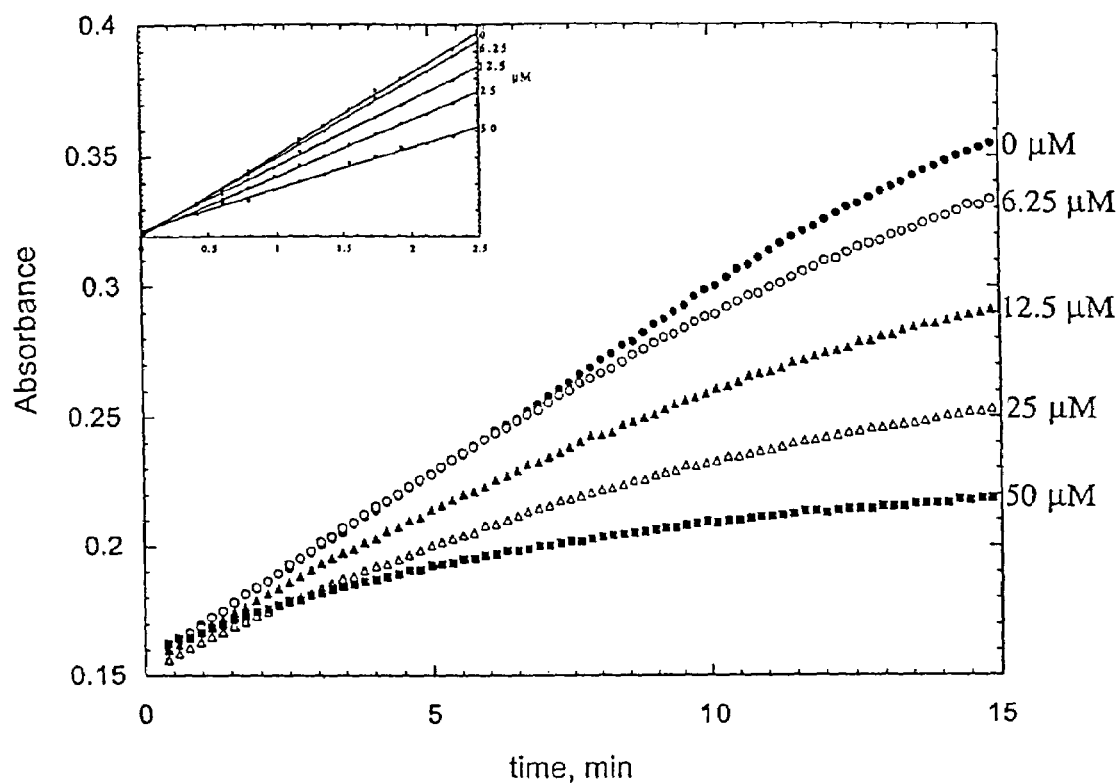
FIG. 8 illustrates absorbance curves at 295 nm for cuvettes containing 1 ml of 100 μM NGD$^+$ (20 times K$_m$) and 0, 6.125, 12.5, 25, and 50 μM nicotinamide 2-deoxyribose. Reactions were started by addition of 2 μl of CD38 (6 mM). Initial slopes were used to determine K$_i$ (FIG. 3), and the points were fitted to the equation $A(t)=vt+(b-v)(1-\exp(-kt))/k+A_0$, where k is the observed rate constant, b is the initial rate, v is the final rate, and A$_0$ is the initial absorbance. As the inset shows, the initial absorbance points of the main curves were used to determine the value of K$_i$. Inhibitor concentrations are shown to the right.

The mechanism of inhibition of βNdR was suspected to be covalent inactivation of CD38, based upon the proposition that CD38 forms a covalent intermediate in the reaction with the substrate $NAD^+$ (FIG. 4) (12). The kinetic features of this inhibition are similar to those for slow-binding inhibitors, where the initial binding of inhibitor is characterized by a $K_i$ value and a subsequent chemical conversion process governed by a rate constant ($k_{chem}$) analogous to the slow-binding step (19). This mechanism of inhibition was tested by treatment of CD38 with different concentrations of inhibitor in the presence of 50 $K_m$ of substrate to establish values for $K_i$ and $k_{chem}$. In the presence of 100 µM $NGD^+$, reaction mixtures containing 0 to 50 µM βNdR were initiated by addition of enzyme (FIG. 8). The initial slopes in FIG. 8 were used to determine a $K_i$ value of 1 µM—the inherent binding affinity of the enzyme for βNdR. The rate curves in FIG. 8 are consistent with competitive inhibition during initial rate measurements, but show increasing inhibition over time. This second phase, showing increased inhibition, reflects conversion of the initial bound inhibitor to a more stable form, proposed to be the chemical reaction of the inhibitor to form an enzyme covalent complex. The fits of these curves determine a rate constant for chemical reaction: a $k_{chem}$ of 0.0126 $s^{-1}$ and a $t_{1/2}$ for inactivation of 55 sec (FIG. 4).

C. Reversibility of βNdR Inhibition

Recovery of CD38 catalytic activity after inhibition by βNdR was measured by adding inactivated CD38 to solutions of $NGD^+$, and monitoring absorbance change at 295 nm for periods of 3-4 h. The recovery process was slow: full catalytic activity was not restored over this time period. However, the measured rate constant for recovery could be measured by regressive fit of the data to the activity recovery equation, $A(t)=vt+(b-v)(1-\exp(-k_{off}t))/k_{off}+A_0$, where $k_{off}$ is the observed rate constant, b is the initial rate, v is the final rate, and $A_0$ is the initial absorbance. These data produced a $k_{off}$ value of $5\times10^{-6}$ $sec^{-1}$, to give a $t_{1/2}$ for recovery of 38 h. The proposed mechanism of recovery operates through the hydrolytic path (FIG. 4).

D. Product-Assisted Rescue of Inactivated CD38

Figure 5:
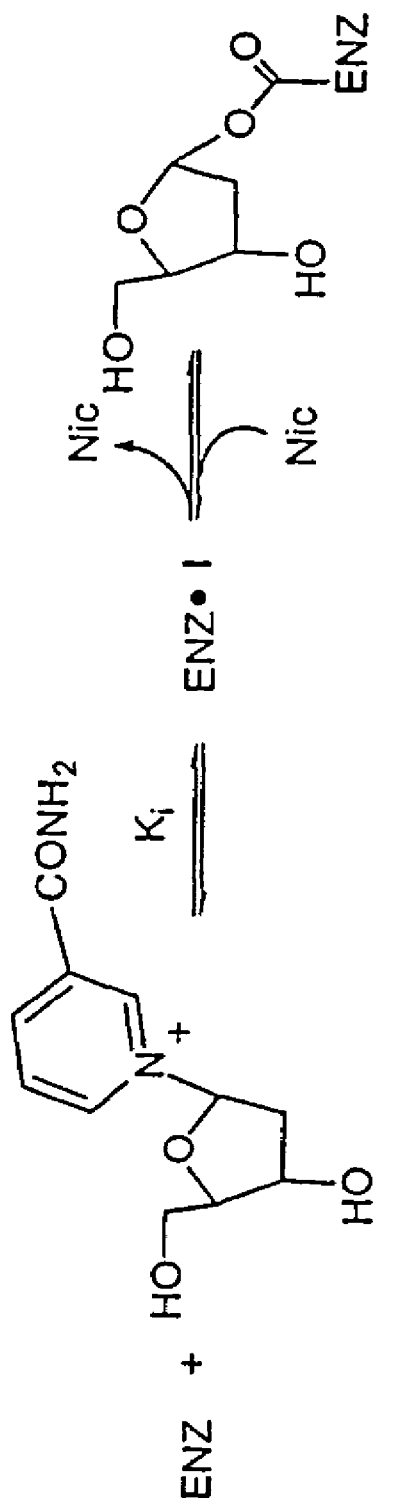
FIG. 5 sets forth the proposed mechanism of rescue of inhibited CD38 by nicotinamide, through the exchange reaction.

Chemical inactivation of CD38 by βNdR can be rapidly reversed by exposure of the inhibited enzyme to millimolar concentrations of nicotinamide. Inhibited enzyme that was treated with 20 mM nicotinamide for 5 min, then diluted into $NGD^+$ and assayed, exhibited complete recovery of catalytic activity, as compared with a control. The mechanism of recovery is shown in FIG. 5. A nicotinamide base-exchange reaction is catalyzed by CD38, with its normal substrates, in the presence of millimolar concentrations of base. Thus, covalent inactivation can be reversed by nicotinamide reaction with the covalent complex, through the normal exchange pathway. This result is diagnostic for a covalent intermediate, as is the mechanism of inhibition of CD38 by βNdR.

E. Inhibition Efficiency for βNdR

Kinetic parameters for βNdR inhibition, inactivation, and recovery provide a complete rate profile for the inhibition-recovery process (Table 2). The values of $k_{on}$, $K_i$, $k_{chem}$, and $k_{off}$ can be used to assess the value of $K_{ieff}$, as defined by either $K_i k_{off}/k_{chem} = K_{ieff}$ or $k_{off}/k_{on} = K_{ieff}$. Table 2 shows that $K_{ieff}$ values agree reasonably well, regardless of approach taken. The value derived from the former method of calculating $K_{ieff}$ is 0.4 nM, whereas the $K_{ieff}$ values calculated by the latter method are 3.2 and 5.0 nM. Averaging these separate values for $K_{ieff}$ yields a value of 2.9±2.3 nM. The data establish that βNdR is a potent inhibitor of CD38.

TABLE 2

Kinetic and thermodynamic parameters for the inhibition of CD38 by β-1'-nicotinamide-2'-deoxyribose.

| Parameter | value | Error | Method |
|---|---|---|---|
| $k_{on}$ | 1100 $M^{-1} s^{-1}$ | | Activity decay |
| $k_{on}$ | 1500 $M^{-1} s^{-1}$ | | Radioactivity |
| $K_i$ | 2.5 μM | | Competitive |
| $k_{chem}$ | 0.0126 $s^{-1}$ | | Competitive onset |
| $k_{off}$ | 5.0 × $10^{-6}$ $s^{-1}$ | | Activity recovery |
| $K_{ieff}$ | 5.1 × $10^{-9}$ M | | Activity, $k_{off}^1$ |
| $K_{ieff}$ | 3.3 × $10^{-9}$ M | | Radioactivity, $k_{off}^1$ |
| $K_{ieff}$ | 4.0 × $10^{-10}$ M | | Competitive, $k_{off}^2$ |
| $K_{ieff}$ | 2.9 × $10^{-9}$ M | ±2.3 | Average of values |

$^1 K_{ieff} = k_{off}/k_{on}$;
$^2 K_{ieff} = K_i k_{off}/k_{chem}$

F. Mechanistic Interpretation

Figure 9:
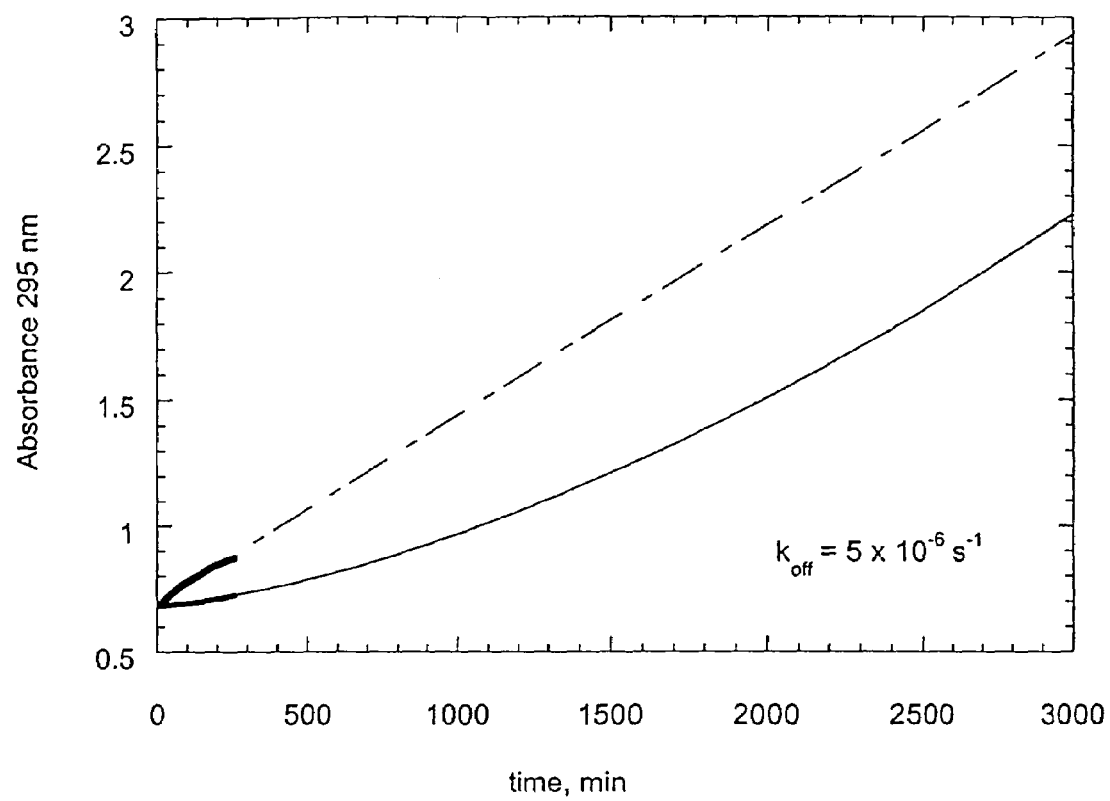
FIG. 9 sets forth absorbance curves showing recovery of CD38 activity after complete inhibition by nicotinamide deoxyribose, as compared with the control. The bottom curve was fitted to the equation $A(t)=vt+(b-v)(1-\exp(-kt))/k+A_0$, where k is the observed rate constant, b is the initial rate, v is the final rate, and A$_0$ is the initial absorbance.

Evaluation of the inhibitor at substrate concentrations that approximate 50×$K_m$ shows that the inhibitor is efficiently recognized by CD38 with a $K_i$ value of 1.0 μM (FIG. 8, inset). This $K_i$ value is surprising, given that the $K_m$ value for the NGD$^+$ substrate is 2 μM. The subsequent onset of more potent inhibition over time is consistent with the subsequent chemical inactivation of the enzyme (FIGS. 3 and 8). The covalent nature of this second phase of inhibition (analogous to slow-binding) is demonstrated through the ability to rescue CD38 from inhibition by adding millimolar concentrations of nicotinamide (FIGS. 5 and 9). The covalent inactivation process is governed by an intrinsic rate constant, $k_{chem} = 0.0126$ $\sec^{-1}$ (FIG. 4).

In the absence of nicotinamide, the inhibition of CD38 by βNdR is limited by a slow recovery of enzymatic activity that is governed by the rate constant for hydrolysis, $k_{off} = 5 \times 10^{-6}$ $\sec^{-1}$ (FIG. 4). This number can be compared directly with the $k_{cat}$ for NMN$^+$ hydrolysis, since hydrolysis of the covalent intermediate was measured to be 512 $\sec^{-1}$ at 37° C. (11). The rate of CD38-deoxyribose hydrolysis is $10^{-8}$ that of CD38 ribose 5-phosphate, implicating the 2'-OH as a proton transfer agent. Substrates for the first step of the reaction, which lack the hydroxyl (OH) group, generate relatively stable intermediates; thus, they provide potent inhibition of the CD38 enzyme. The presence of an electronegative atom is neither necessary nor essential to the development of effective inhibitors for CD38. The synthesis of a new generation of mechanism-based inhibitors for ADP-ribosyl transferases is possible, based on the above-described mechanism of catalysis.

G. Inhibition of CD38 by 1'-pyridyl-deoxy-ribose and 5'-phospho-1'-pyridyl-deoxyribose The ability of CD38 to tolerate changes in the NAD$^+$ structure, specifically at the site of the nicotinamide ring, has been previously investigated (27). This work showed that there is a strong correlation between $\log k_{cat}$ and the $pK_a$ value of the corresponding pyridyl leaving group, with a heightened "above-the-line" value of $\log k_{cat}$ for nicotinamide, reflecting optimization of the enzyme for the natural substrate. The design of inhibitors, then, should be flexible, based upon these observations. Synthesis of pyridyl deoxyribose derivatives was accomplished to prove that inhibition of CD38 can be achieved by changing the leaving-group structure.

Incubation of CD38 with 50 μM to 50 mM concentrations of pyridyl-deoxyribose in the presence of 5 μM (3 $K_m$) NGD$^+$ gave a $K_i$ value for CD38 inhibition by pyridyl-deoxyribose of 11 mM. The low affinity of this structure versus that of the nicotinamide derivative (1 μM) no doubt reflects the loss of hydrogen bonding as a consequence of the omission of the amide group as a pyridine-ring substituent. Onset of covalent inactivation is also very much slower than the βNdR rate of onset. At saturating concentrations (25 mM) in the absence of NGD$^+$, β-pyridyl-deoxyribose covalently inactivated CD38 at a rate of $1.7 \times 10^{-4}$ $s^{-1}$, equivalent to the value of $k_{chem}$. Achievement of only 60-80% inhibition was obtained due to long onset times and inhibitor decomposition. However, the extent of inhibition was confirmed by gel-filtration using radiolabeled [2'-3H]β-pyridyl-deoxyribose, where the extent of inhibition determined by activity assay correlated to the quantity of radiolabeled enzyme eluting from the column (see Experimental Details). The calculated value for $K_{ieff}$ ($k_{off} K_i / k_{chem}$) = 323 μM, which was $10^5$ times larger than the value of $K_{ieff}$ for βNdR (2 nM). The considerably greater inhibition value reflects lowered binding affinity and the lower rate of chemical inactivation. The diminished value of $k_{chem}$ versus that for βNdR ($1.7 \times 10^{-4}$ $s^{-1}$ versus $1.3 \times 10^{-2}$ $s^{-1}$) almost completely reflects the predicted loss of rate based upon the $pK_a$ differences of the leaving groups: ($pK_{a\ pyridine} - pK_{a\ nicotinamide} = 1.5$ versus $\log k_{chem(nicotinamide)} / \log k_{chem\ (pyridine)} = 1.86$).

Similar studies were performed for the inhibition of CD38 by the 5'-phospho-1'-pyridyl-deoxyribose derivative. The determined value for $K_i > 200$ μM reflects a relatively weak intrinsic binding affinity of the structure for the enzyme. This valuation underscores the significance to binding affinity of the amide structure of the pyridyl ring of nicotinamide, which cannot be overcome by addition of the 5'phosphoryl moiety. This fact is indicated by a comparison to the $K_i$ value for βNdR (1 μM). Extended incubations of CD38 with 200 μM 5'-phospho-1'-pyridyl-deoxyribose inhibited the enzyme. Plots of activity versus time determined a minimum value for $k_{chem}$ of $2.2 \times 10^{-4}$ $s^{-1}$. Use of [2'-$^3$H]5'-phospho-1'-pyridyl-deoxy-ribose as inhibitor confirmed covalent attachment of the sugar moiety to the enzyme by the gel-filtration approach (see Experimental Details).

4. Conclusion

Mechanism-based inhibitors are specific and efficient when they undergo rapid conversion to an enzymatic covalent intermediate that is slow in achieving subsequent steps. An understanding of this strategy has led to the development of novel inhibitors of CD38. Enzymes that share catalytic site homology with CD38, such as human bone stromal cell antigen (humBST1), are also expected to be targets for these agents. The use of 1-substituted-2-deoxyribose is a new development that is based on the detailed mechanism of CD38 and related enzymes. The deoxy analogues support a mechanism in which removal of the 2'-OH moiety leads to potent inhibition, without a requirement for an electronegative atom at the 2'-position. Hurdles toward the synthesis of these molecules have been overcome by the development of a new and flexible synthetic methodology. Efficient synthesis of various pyridyl-substituted nucleosides in high yield and high stereoselectivity is now possible. The enzymes that can be inhibited by deoxy pyridyl compounds are CD38, the human ADP-ribosyl cyclase, invertebrate and plant ADP-ribosyl cyclases, and possibly several other ADP-ribosyl transferases involved in the regulation of gene expression (e.g., SIR family enzymes and their homologues).

REFERENCES

1. Jackson and Bell, *Immunol.*, 144:2811-15, 1990.
2. Mehta et al., *FASEB J.*, 10:1408-17, 1996.
3. Lee et al., *J. Biol. Chem.*, 264:1608-15, 1989.
4. Prasad et al., *Nat. Struct. Biol.*, 3:957-64, 1996.
5. Lee et al., *Nature Struct. Biol.*, 1:143-44, 1994.
6. Reyes-Harde et al., *Proc. Natl. Acad. Sci.*, 96:4061-66, 1999.
7. Galione et al., *Science*, 253:1143-46, 1991.
8. Wu et al., *Science*, 278:2126-30, 1997.
9. Okamoto, H., *Mol. Cell. Biochem.*, 193:115-18, 1999.
10. Cockayne et al., *Blood*, 92:1324-33, 1998.
11. Sauvé et al., *Biochemistry*, 37:13, 239-49, 1998.
12. Sauvé et al., *J. Am. Chem Soc.*, 122:7855-59, 2000.
13. Muller-Steffner et al., *J. Biol. Chem.*, 271:23, 967-72, 1996.
14. Berthelier et al., *Biochem. J.*, 330:1383-90, 1998.
15. Kim et al., *Science*, 261:1330-33, 1993.
16. Fox et al., *J. Am. Chem Soc.*, 83:4066-70, 1961.
17. Munshi et al., *Methods Enzymol.*, 280:318-30, 1997.
18. Niedballa and Vorbruggen, *J. Org. Chem.*, 39:3654-60, 1974.
19. Morrison and Walsh, *Adv. Enzymol. Relat. Areas Mol. Biol.*, 61:201-301, 1988.
20. Porter et al., *J. Biol. Chem.*, 270:15, 551-56, 1995.
21. Zechel and Withers, *Acc. Chem Res.*, 33:11-18, 2000.
22. Wong et al., *J. Biol. Chem.*, 273:34, 057-62, 1998.
23. Withers and Street, *J. Am. Chem. Soc.*, 110:8551-53, 1988.
24. Sleath et al., *J. Org. Chem.*, 56:3608-13, 1991.
25. Muller-Steffner et al., *J. Biol. Chem.*, 267:9606-11, 1992.
26. Oppenheimer and Handlon, *The Enzymes*, 20:454-505, 1992.
27. Berthelier et al., *Eur. J. Biochem.*, 267(10):3056-64, 2000.
28. Kang et al., *Nucleosides Nucleotides* 17:1089, 1998.
29. Jiang et al., *J. Biol. Chem.*, 273:11, 017, 1998.
30. Li et al., *Tetrahedron*, 53: 12, 017, 1997.
31. Kruppa et al., *Bioorg. Med. Chem. Lett.*, 7:945, 1997.
32. Merkler et al., *Biochemistry*, 29:8358-64, 1990.
33. Lund et al., *Immunol. Rev.*, 161:79-93, 1998.
34. Clapper et al., *J. Biol. Chem.*, 262:9561-68, 1987.
35. Lee and Aarhus, *Cell Regul.*, 2:203-09, 1991.
36. States et al., *Trends Biochem. Sci.*, 17:495, 1992.
37. Howard et al., *Science*, 262:1056-59, 1993.
38. Lee et al., *Mol. Cell. Biochem.*, 193:89-98, 1999.
39. Lee, H. C., *Recent Prog. Horm. Res.*, 51:355-88, 1996.
40. Lee, H. C., *Physiological Rev.*, 77:1133-64, 1997.
41. Lee, H. C., *Cell. Biochem. Biophys.*, 28:1-17, 1998.
42. Lee et al., *Vit. Horm.*, 48:199-257, 1994.
43. Lee, H. C., *Mol. Cell. Biochem.*, 138:229-35, 1994.
44. Lee et al., *Nature*, 307-09, 1994.
45. Sun et al., *Cell. Biol.*, 146:1161-71, 1999.

All publications mentioned hereinabove are hereby incorporated in their entireties. While the foregoing invention has been described in some detail for purposes of clarity and understanding, it will be appreciated by one skilled in the art, from a reading of the disclosure, that various changes in form and detail can be made without departing from the true scope of the invention in the appended claims.

What is claimed is:

1. A compound represented by the formula:

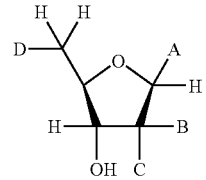

wherein
A is —S—Y or —O—Y, wherein Y is a substituted phenyl group, a substituted pyridyl group, a nicotinamide group, or a hydroxy-substituted nicotinamide group and wherein the phenyl group is substituted with a halogen, thiol, amino, oxygen or carboxyamine;
B is hydrogen, or a halogen, or an amino group;
C is hydrogen, or a halogen, or an amino group; and
D is a primary alcohol, a hydrogen, or an oxygen, nitrogen, carbon, or sulfur linked to phosphate, a phosphoryl group, a pyrophosphoryl group, or adenosine monophosphate through a phosphodiester or carbon-, nitrogen-, or sulfur-substituted, phosphodiester bridge, or to adenosine diphosphate through a phosphodiester or carbon-, nitrogen-, or sulfur-substituted pyrophosphodiester bridge.

2. The compound of claim 1, wherein A is —O—Y.

3. The compound of claim 1, wherein A is —S—Y.

4. The compound of claim 2, wherein both B and C are hydrogen, or either B or C is a halogen or an amino group and the other of B or C is hydrogen.

5. The compound of claim 3, wherein both B and C are hydrogen, or either B or C is a halogen or an amino group and the other of B or C is hydrogen.

6. The compound of claim 2, wherein D is a primary alcohol or hydrogen.

7. The compound of claim 3, wherein D is a primary alcohol or hydrogen.

8. The compound of claim 1, wherein both B and C are hydrogen, or either B or C is a halogen or an amino group and the other of B or C is hydrogen.

9. The compound of claim 1, wherein D is a primary alcohol or hydrogen.

* * * * *

UNITED STATES PATENT AND TRADEMARK OFFICE
CERTIFICATE OF CORRECTION

| | | |
|---|---|---|
| PATENT NO. | : 7,504,489 B2 | |
| APPLICATION NO. | : 11/294932 | |
| DATED | : March 17, 2009 | |
| INVENTOR(S) | : Anthony A. Sauvé and Vern L. Schramm | |

It is certified that error appears in the above-identified patent and that said Letters Patent is hereby corrected as shown below:

In the specification

Column 1, lines 10-15, should read:

-- STATEMENT OF GOVERNMENT SUPPORT

This invention was made with government support under grant numbers AI034342 and GM019335 awarded by the National Institutes of Health. The government has certain rights in the invention. --

Signed and Sealed this
Twenty-ninth Day of December, 2015

Michelle K. Lee
*Director of the United States Patent and Trademark Office*